(12) United States Patent
Kumble

(10) Patent No.: US 10,948,486 B2
(45) Date of Patent: *Mar. 16, 2021

(54) ASSAY MEMBRANE AND METHOD OF USE THEREOF

(71) Applicant: Pictor Limited, Auckland (NZ)

(72) Inventor: Sarita Kumble, Auckland (NZ)

(73) Assignee: Pictor Limited, Auckland (NZ)

( * ) Notice: Subject to any disclaimer, the term of this patent is extended or adjusted under 35 U.S.C. 154(b) by 237 days.

This patent is subject to a terminal disclaimer.

(21) Appl. No.: 15/490,795

(22) Filed: Apr. 18, 2017

(65) Prior Publication Data

US 2018/0067109 A1 Mar. 8, 2018

Related U.S. Application Data

(63) Continuation of application No. 12/513,659, filed as application No. PCT/US2007/082732 on Oct. 26, 2007, now Pat. No. 9,625,453.

(Continued)

(51) Int. Cl.
*G01N 33/543* (2006.01)
*B01L 3/00* (2006.01)

(52) U.S. Cl.
CPC ...... *G01N 33/54306* (2013.01); *B01L 3/5025* (2013.01); *B01L 3/5085* (2013.01);
(Continued)

(58) Field of Classification Search
CPC ........... G01N 33/54306; G01N 33/543; G01N 2800/52; B01L 3/5025; B01L 3/5085; B01L 3/50855
See application file for complete search history.

(56) References Cited

U.S. PATENT DOCUMENTS 6,417,324 B1 7/2002 Sallberg
6,699,665 B1 3/2004 Kim et al.
(Continued)

FOREIGN PATENT DOCUMENTS

CA 2509063 6/2004
CA 2606815 A1 11/2006
(Continued)

OTHER PUBLICATIONS

Bangham et al.:. "*Protein microarray-based screening of antibody specificity*"; Methods Mol. Med., 2005, 144: 173-182.
(Continued)

*Primary Examiner* — Gailene Gabel
(74) *Attorney, Agent, or Firm* — DLA Piper LLP (US)

(57) ABSTRACT

The present invention provides a microporous membrane for detecting at least one target analyte in a sample. The membrane includes an array that comprises at least one capture element and at least one control element printed on the membrane surface, at least one capture element corresponding to and being able to bind a target analyte, the plurality of control elements, when present including:
 i) at least one fiduciary marker,
 ii) at least one negative control to monitor background signal,
 iii) at least one negative control to monitor assay specificity,
 iv) at least one positive colorimetric control, and
 v) at least one positive control to monitor assay performance or any combination thereof.

20 Claims, 5 Drawing Sheets

Related U.S. Application Data

(60) Provisional application No. 60/861,771, filed on Nov. 28, 2006.

(52) U.S. Cl.
CPC ........ *B01L 3/50855* (2013.01); *G01N 33/543* (2013.01); *G01N 2800/52* (2013.01)

(56) References Cited

U.S. PATENT DOCUMENTS

| | | | |
|---|---|---|---|
| 7,074,194 | B2 | 7/2006 | Crosby et al. |
| 9,625,453 | B2* | 4/2017 | Kumble ............ G01N 33/54306 |
| 2003/0026739 | A1* | 2/2003 | MacBeath ............ B01J 19/0046 422/417 |
| 2003/0109420 | A1 | 6/2003 | Valkirs et al. |
| 2003/0153013 | A1* | 8/2003 | Huang ................... C40B 30/04 435/7.9 |
| 2004/0191810 | A1 | 9/2004 | Yamamoto |
| 2005/0003398 | A1 | 1/2005 | Tao |
| 2005/0153381 | A1 | 7/2005 | Marusich et al. |
| 2005/0211559 | A1 | 9/2005 | Kayyem |
| 2006/0024703 | A1* | 2/2006 | Zhang ................... C12Q 1/6837 435/6.11 |
| 2007/0225206 | A1 | 9/2007 | Ling et al. |
| 2009/0118133 | A1 | 5/2009 | Melrose |

FOREIGN PATENT DOCUMENTS

| | | |
|---|---|---|
| CA | 2664108 A1 | 3/2008 |
| WO | WO 2000/005579 A1 | 2/2000 |
| WO | WO 2005/093419 A1 | 10/2005 |

OTHER PUBLICATIONS

Canadian Office Action regarding application 2,670,615.
Haab: "*Methods and applications of antibody microarrays in cancer research*"; Proteomics, 2003, 3: 2116-2122.
Huang et al.: "*Simultaneous detection of multiple cytokines from conditioned media and patient's sera by an antibody-based protein array system*"; Analytical Biochemistry, 2001, 294: 55-62.
Invitrogen,. "*ProtoArray® Applications Guide*"; ThermoFischer Scientific, 2015, 136 pages.
Kastenbauer et al.: "*Patterns of protein expression in infectious meningitis: a cerebrospinal fluid protein array analysis*"; J. Neuroimmunol., 164(1-2):134-139 (2005).
Kokubun et al.: "*Serum Amyloid A (SAA) concentrations varies among rheumatoid arthritis patients estimated by SAA/CRP ratio*"; Clinica Chimica Acta, 360: 97-102 (2005).
Li et al.: "*Protein array method for assessing in vitro biomaterial-induced cytokine expression*"; Biomaterials, 26(10)1081-1085 (2005).
Masters et al.: "*Diagnostic challenges for multiplexed protein microarrays*"; Drug Discovery Today, Nov. 2006, 11: 1007-1011.

* cited by examiner

ASSAY MEMBRANE AND METHOD OF USE THEREOF

CROSS-REFERENCE TO RELATED APPLICATIONS

This application is a continuation application of U.S. application Ser. No. 12/513,659 filed Dec. 16, 2009, now issued as U.S. Pat. No. 9,625,453; which is a 35 USC § 371 National Stage application of International Application Serial No. PCT/US2007/082732 filed Oct. 26, 2007, now expired; which claims the benefit under 35 USC § 119(e) to U.S. Application Ser. No. 60/861,771 filed Nov. 28, 2006. The disclosure of each of the prior applications is considered part of and is incorporated by reference in the disclosure of this application.

BACKGROUND OF THE INVENTION

Field of the Invention

The present invention relates to a method for the colorimetric detection of at least one analyte in a sample, preferably multiple analytes in a sample, and membranes for use in the method.

Background Information

Biomarkers can identify disease prior to exhibition of clinical symptoms by a subject, and therefore provide the ability to treat the molecular basis of disease using targeted therapies. Thus, biomarkers allow the pharmacodynamic effects of targeted therapeutics to be evaluated before clinical signs and symptoms become evident.

New biomarkers are being discovered by means of a large number of proteomic and genomic studies using low throughput, labour intensive technologies such as mass spectrometry and high performance liquid chromatography. These technologies are great discovery tools for identifying novel biomarkers in small numbers of samples from subjects. However, biomarkers must be qualified by testing large numbers of samples from subjects before being accepted as a clinically valid biomarker. Currently available technologies for screening large numbers of samples from subjects are expensive and cumbersome.

Colorimetric immunoassays are often considered the accepted standard for single protein measurement. These assays typically involve a primary antigen-specific antibody to bind the target antigen from the sample, with antigen binding detected using a secondary antibody linked to a colorimetric detection system. The most widely used format is enzyme-linked immunosorbent assays (ELISA), having well-established protocols for the measurement of single proteins in solutions.

There is a need for simple, rapid and cost-effective diagnostic tests that can be used to detect biomarkers in biological samples. The increasing interest in the simultaneous measurement of multiple proteins in samples has lead to the development of multiplexed immunoassays in a microarray format. Protein-based microarrays are currently used for a variety of applications. However, this technology has yet to be adopted as a routine method for diagnostic testing, due to technical challenges surrounding the sensitivity, specificity and cross-reactivity of the assay reagents and the need for expensive instrumentation. Accordingly, technologies are needed that can rapidly develop and implement assay methods adapted for high throughput, scalable and cost-effective screening to validate the utility of biomarkers across large segments of the population.

SUMMARY OF THE INVENTION

One aspect of the invention relates to a microporous membrane for detecting at least one target analyte in a sample, the membrane comprising an array that comprises at least one capture element and optionally a plurality of control elements spotted, printed or the like, onto the membrane surface, the at least one capture element corresponding to and being able to bind a target analyte. The plurality of control elements, when optionally included, may comprise:
  a) at least one fiduciary marker,
  b) at least one negative control to monitor background signal,
  c) at least one negative control to monitor assay specificity,
  d) at least one positive colourimetric control, and
  e) at least one positive control to monitor assay performance or any combination thereof.

While the present invention is described with reference to use of colourimetry and colourimetric controls, it should be understood that other detection systems may be employed. For example, fluorescent dyes such as Texas Red and enzyme substrates that generate a chemiluminescent signal may be used.

Another aspect of the invention relates to a microporous membrane for detecting a plurality of target analytes in a sample, the membrane comprising an array of capture elements printed on the membrane surface, each capture element corresponding to and being able to bind a target analyte. Optionally, the array may further include a plurality of control elements comprising:
  a) at least one fiduciary marker,
  b) at least one negative control to monitor background signal,
  c) at least one negative control to monitor assay specificity,
  d) at least one positive colourimetric control, and
  e) at least one positive control to monitor assay performance or any combination thereof.

In one embodiment the array of capture elements comprises a plurality of groups of capture elements, each capture element within a group being able to bind the same target analyte, and each group of capture elements being able to bind a different target analyte than any other group of capture elements. In an alternative embodiment the array of capture elements comprises a plurality of pairs of capture elements, each capture element in a pair being able to bind the same target analyte, each pair of capture elements being able to bind a different target analyte than any other pair of capture elements.

In one embodiment, the plurality of groups of capture elements are able to bind a plurality of target analytes, wherein the plurality of target analytes comprises one or more panels of target analytes indicative of one or more human diseases or conditions as set forth in Table 1. In an alternative embodiment, the plurality of groups of capture elements are able to bind a plurality of target analytes, wherein the plurality of target analytes comprises one or more panels of target analytes determines the efficacy of one or more treatments as set forth in Table 2. In another alternative embodiment, the plurality of groups of capture elements are able to bind a plurality of target analytes, wherein the plurality of target analytes comprises one or more panels of target analytes for animal testing as set forth in Table 3. In another alternative embodiment, the plurality of target analytes represent a combination of any two or more panels as set forth in Tables 1-3.

In one embodiment the target analyte is selected from a protein, a protein fragment, a peptide, a polypeptide, a polypeptide fragment, an antibody, an antibody fragment, an antibody binding domain, an antigen, an antigen fragment, an antigenic determinant, an epitope, a hapten, an immunogen, an immunogen fragment, a metal ion, a metal ion-coated molecule, biotin, avidin, streptavidin, an inhibitor, a co-factor, a substrate, an enzyme, a receptor, a receptor fragment, a receptor subunit, a receptor subunit fragment, a ligand, a receptor ligand, a receptor agonist, a receptor antagonist, a signalling molecule, a signalling protein, a signalling protein fragment, a growth factor, a growth factor fragment, a transcription factor, a transcription factor fragment, an inhibitor, a monosaccharide, an oligosaccharide, a polysaccharide, a glycoprotein, a lipid, a cell, a cell-surface protein, a cell-surface lipid, a cell-surface carbohydrate, a cell-surface glycoprotein, a cell extract, a virus, a virus coat protein, a hormone, a serum protein, a milk protein, an oligonucleotide, a macromolecule, a drug of abuse, or any combination of any two or more thereof.

In one embodiment the capture element is selected from a protein, a protein fragment, a binding protein (BP), a binding protein fragment, an antibody, an antibody fragment, an antibody heavy chain, an antibody light chain, a single chain antibody, a single-domain antibody (a VHH for example), a Fab antibody fragment, an Fc antibody fragment, an Fv antibody fragment, a F(ab')2 antibody fragment, a Fab' antibody fragment, a single-chain Fv (scFv) antibody fragment, an antibody binding domain, an antigen, an antigenic determinant, an epitope, a hapten, an immunogen, an immunogen fragment, a binding domain; a metal ion, a metal ion-coated molecule; biotin, avidin, streptavidin; a substrate, an enzyme, an abzyme, a co-factor, a receptor, a receptor fragment, a receptor subunit, a receptor subunit fragment, a ligand, an inhibitor, a hormone, a binding site, a lectin, a polyhistidine, a coupling domain, an oligonucleotide, or a combination of any two or more thereof.

In one embodiment the capture element is an antibody or antibody fragment and the target analyte is an antigen. In another embodiment the capture element is an antigen and the target analyte is an antibody or antibody fragment.

In one embodiment the target analyte is an antigen associated with a disease or disorder, such as an infectious disease, allergic disease, autoimmune disease, cardiac disease, cancer or graft versus host disease.

In another embodiment the target analyte is a blood contaminant for testing blood bank samples, a compatibility determinant for assessing transplant rejection, an analyte indicative of pregnancy (such as human chorionic gonadotropin, hCG) or fertility, a drug or hormone present in a body fluid, a cell activation marker such as a growth factor, a cytokine or a chemokine.

In another embodiment the target analyte is an antibody associated with a disease or disorder, such as an infectious disease, allergic disease, autoimmune disease, cardiac disease, cancer, graft versus host disease, or organ transplant rejection.

In one embodiment the membrane is a nitrocellulose, nylon, polyvinylidene difluoride, polyester, polystyrene, polyethersulfone, cellulose acetate, mixed cellulose ester or polycarbonate membrane.

In one embodiment the membrane is removably attached to a bottomless microtiter plate.

In one embodiment the fiduciary marker is a dye, dye-conjugated protein or chromogenic protein, hapten-conjugated protein or enzyme-conjugated protein; for example, Coomassie Blue, colloidal gold, Ponceau S, a peroxidase enzyme such as horseradish peroxidase (HRP), or a dyed molecular weight marker. Preferably the fiduciary marker permits orientation and gridding of the array.

The array contained on the membrane of the invention, whether through spotting, printing or other methods known to those of skill in the art, typically comprises a plurality of controls including, for example, at least one negative control to monitor background signal, at least one negative control to monitor assay specificity, at least one positive colourimetric control, and at least one positive control to monitor assay performance.

In one embodiment the negative control to monitor background signal is print buffer.

In one embodiment the negative control to monitor assay specificity comprises one or more antibody isotypes, a corresponding antibody or antibody isotype from a different animal species or a closely related ligand.

In one embodiment the positive colourimetric control is an enzyme capable of reacting with a substrate to generate a detectable result. In one embodiment the enzyme label comprises horseradish peroxidase, alkaline phosphatases, β-D-galactosidase or glucose oxidase. In one embodiment the colourimetric control comprises the same colourimetry system used to resolve positive capture element-target analyte binding.

In one embodiment the positive control to monitor assay performance comprises one binding partner of a complementary binding pair, wherein the other binding partner is a sample component or an assay reagent. The assay performance control is preferably selected from a target analyte, a binding partner corresponding to and able to bind a non-target analyte that will be present in the sample, a binding partner corresponding to and able to bind an assay reagent, and a colourimetric enzyme label, or any combination of any two or more thereof.

In another embodiment the array comprises 1, 2, 3 or 4 positive controls to monitor assay performance. In a preferred embodiment the array comprises at least 3 positive controls to monitor assay performance.

In one embodiment each element on the array is printed as a discrete area of between 100 μm to 500 μm in diameter. Preferably each discrete area is between 350 μm to 400 μm in diameter.

In one embodiment the discrete areas of the array are printed in a 5×5 grid but any array format is useful within the scope of the invention. It is not necessary that the array be symmetrical.

In one embodiment four or more different capture elements are printed in the array. In another embodiment, at least two replicates of each capture element are printed in the array.

Another aspect of the invention relates to a microporous membrane for detecting a plurality of target antigens or antibody ligands in a sample, the membrane comprising an array of capture elements printed on the membrane surface, each capture element corresponding to and being able to bind a target antigen or antibody ligand, the capture elements comprising an antibody or antibody fragment. The array may further comprise a plurality of control elements including:
 a) at least one fiduciary marker,
 b) at least one negative control to monitor background signal, c) at least one negative control to monitor assay specificity,
d) at least one positive colourimetric control, and
e) at least one positive control to monitor assay performance or any combination thereof.

Another aspect of the invention relates to a microporous membrane for detecting a plurality of target antibodies in a sample, the membrane comprising an array of capture elements printed on the membrane surface, each capture element corresponding to and being able to bind a target antibody, the capture elements comprising an antigen or antibody ligand. Optionally, the array may further include a plurality of control elements including:
a) at least one fiduciary marker,
b) at least one negative control to monitor background signal,
c) at least one negative control to monitor assay specificity,
d) at least one positive colourimetric control, and
e) at least one positive control to monitor assay performance or any combination thereof.

Another aspect of the invention relates to a microporous membrane for detecting a plurality of target ligands in a sample, the membrane comprising an array of capture elements printed on the membrane surface, each capture element corresponding to and being able to bind a target ligand, the capture elements comprising a receptor or a receptor subunit. The array optionally further includes a plurality of control elements including:
a) at least one fiduciary marker,
b) at least one negative control to monitor background signal,
c) at least one negative control to monitor assay specificity,
d) at least one positive colourimetric control, and
e) at least one positive control to monitor assay performance or any combination thereof.

Another aspect of the invention relates to a microporous membrane for detecting a plurality of target receptors or receptor subunits in a sample, the membrane comprising an array of capture elements printed on the membrane surface, each capture element being able to bind a target receptor or receptor subunit, the capture elements comprising a receptor ligand or receptor subunit ligand. The array optionally further includes a plurality of control elements including:
a) at least one fiduciary marker,
b) at least one negative control to monitor background signal,
c) at least one negative control to monitor assay specificity,
d) at least one positive colourimetric control, and
e) at least one positive control to monitor assay performance or any combination thereof.

Another aspect of the invention relates to a kit for detecting of a plurality of target analytes in a sample including:
a) at least one membrane as described above, and optionally one or more of
  i) a background reducing reagent (otherwise known as a blocking solution),
  ii) a wash solution,
  iii) one or more antibodies (including antibody-binding protein (BP) conjugates or antibody-enzyme label conjugates or both) for detection of antigens, ligands or antibodies bound to the capture elements or for detection of the positive controls,
  iv) a colorimetric detection system,
  v) software for determination of signal intensity at each spot and analysis of results, and
  vi) a protocol for measuring the presence of analytes in samples and any combination thereof.

In one embodiment the background reducing agent is a protein blocking agent selected from the group comprising skim milk, casein, bovine serum albumin, gelatins from fish, pigs or other species and dextran. The blocking agent may be supplemented with a detergent such as Tween 20, Triton X-100 and CHAPS.

In one embodiment the colourimetric detection system comprises an enzyme label selected from the group comprising horseradish peroxidase, alkaline phosphatases, β-D-galactosidase or glucose oxidase and a substrate selected from the list comprising 3,3',5,5'-tetramethylbenzidine, diaminobenzidine, metal-enhanced diaminobenzidine, 4-chloro-1-naphthol, colloidal gold, nitro-blue tetrazolium chloride, 5-bromo-4-chloro-3'-indolylphosphate p-toluidine salt and naphthol AS-MX phosphate+Fast Red TR Salt.

In another aspect the invention relates to a method of processing a microarray or detecting an analyte in a sample comprising:
a) providing a membrane described above,
b) adding at least one sample to the membrane, and
c) processing the membrane such that a detectable result is given by two or more of
  i) at least one fiduciary marker,
  ii) at least one positive colourimetric control, and
  iii) at least one positive control to monitor assay performance.

In one embodiment the step of processing the membrane comprises a blocking step during which available protein binding sites on the membrane are blocked, an optional wash step, contacting the membrane with the sample containing one or more analytes to be measured, a wash step to remove non-bound material from the membrane, contacting the membrane with one or more secondary antibodies that correspond to and will bind one or more target analytes and non-target analyte that is bound to an assay performance control, an optional wash step, and contacting the membrane with one or both of an enzyme conjugate or an enzyme substrate to generate a detectable result.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

The invention may also be said broadly to consist in the parts, elements and features referred to or indicated in the specification of the application, individually or collectively, in any or all combinations of two or more of said parts, elements or features, and where specific integers are mentioned herein that have known equivalents in the art to which the invention relates, such known equivalents are deemed to be incorporated herein as if individually set forth.

DETAILED DESCRIPTION OF THE INVENTION

Figures 1A, 1B, 1C:
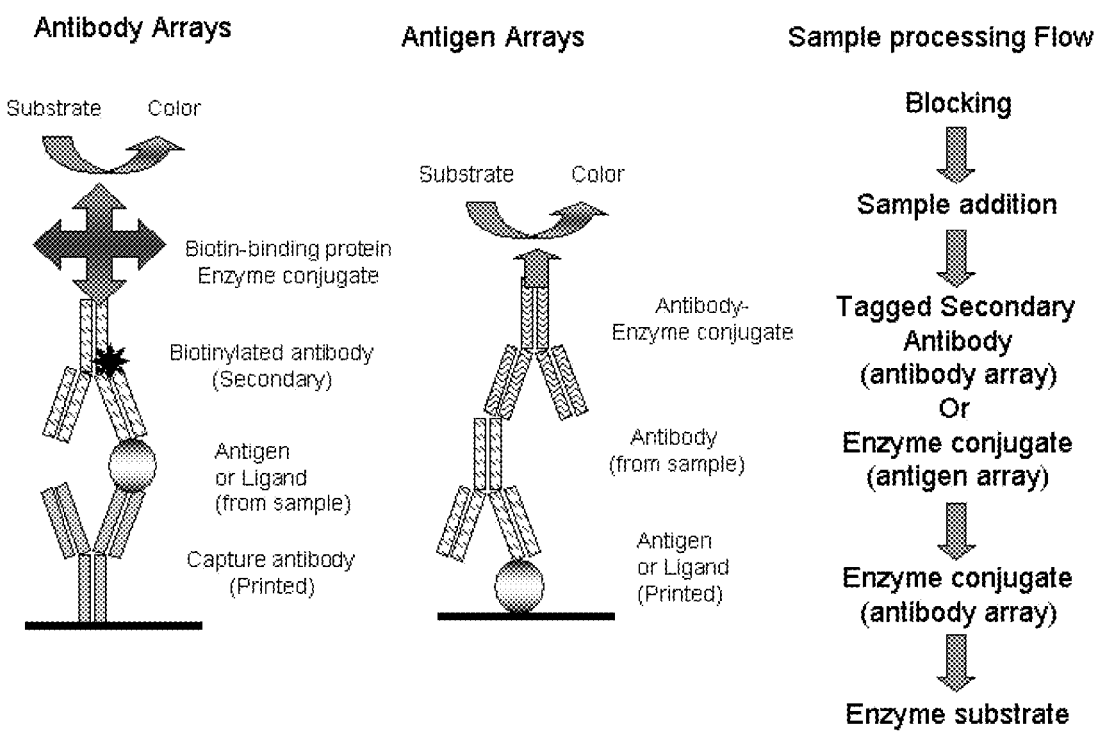
FIG. 1A is a pictorial diagram summarizing the processing of an antibody array of the invention for antigen detection.
FIG. 1B is a pictorial diagram summarizing an antigen array of the invention for antibody detection.
FIG. 1C is a pictorial diagram summarizing the steps for processing a printed array of the invention.

The present invention relates to an assay membrane for detecting of at least one target analyte or a plurality of target analytes in a sample, as well as kits for detecting said target analytes and a method of processing the assay membrane.

Biomarkers can identify disease prior to exhibition of clinical symptoms by a subject, and therefore provide the ability to treat the molecular basis of disease using targeted therapies. The basis for subject stratification lies in correlation of molecular heterogeneity of disease with heterogeneity of response to therapy. As such, the target of the drug must be present and have a role in maintaining or worsening the disease state of the subject in order for the drug to be effective. This target would therefore serve as a biomarker to determine whether the subject is a candidate for treatment with that particular therapy. For example, the presence of Her2/neu in tumors is required for effective treatment with anti-Her2 antibodies, such as Herceptin. Biomarkers can also be used for retrospective sample analysis after clinical trials have been completed or after post-marketing analysis of new drugs to perform subgroup analysis to identify covariates that were expected to account for differences in response.

Accordingly, the present invention contemplates a plurality of capture agents arranged to detect one or more (i.e., a panel) target analytes (i.e., biomarkers) that may be used for a variety of assays. For example, a panel of biomarkers may be monitored during clinical trials to determine effectiveness of therapy while simultaneously ensuring lack of side effects or any other adverse events. Thus, a panel of biomarkers may be used to test a variety of conditions and/or to further validate one or more potential biomarkers. Exemplary conditions include, but are not limited to, human diseases or allergies, pregnancy detection, animal diseases, and animal testing performed prior to export. It should be understood that the panel of biomarkers can be used during all phases of clinical trials to obtain a greater understanding of drug mechanism in a population prior to approval and general administration of the drug. Furthermore, biomarkers can support clinical outcome results from efficacy studies and help to measure real clinical benefit to the subject.

Biomarkers can also be used to determine which subjects are likely to respond to a particular therapeutic. Biomarkers can also be used to monitor disease progression and treatment efficacy by measuring levels of various disease parameters simultaneously, thereby increasing the benefit of treatment to the subject. These biomarker panels aim to identify the right drug for the right subject at the right time.

Biomarker validation for prediction of a particular disease, disorder, or condition refers to the confirmation of accuracy, reproducibility and effectiveness of biomarkers in detecting the disease, disorder or condition. The major challenge for biomarker validation is the high level of variability of biomarker levels across the human population and the considerable molecular heterogeneity of specific diseases, even from a single tissue. As a newly discovered biomarker makes the transition from the research setting to the clinical diagnostic laboratory, it should progress through defined stages of confirmation. The first task of biomarker validation is evaluation of research technology, performance, and specifications (analytical validation). However, the ultimate goal is initial validation of the biomarker to identify early stage diseases, disorders, or conditions (clinical validation). Upon technical and clinical confirmation, assays involving the biomarker are moved systematically toward a standardized, reproducible, high-throughput format for clinical diagnostic implementation. With laboratory performance rigorously established, the clinical variables can subsequently be analyzed to define limitations, applications, and clinical utility.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

The term "biomarker" refers to any substance used as an indicator of a biologic state. Thus, a biomarker can be any substance whose detection indicates a particular disease state (for example, the presence of an antibody may indicate an infection). Furthermore, a biomarker can be indicative of a change in expression or state of a protein that correlates with the risk or progression of a disease, or with the susceptibility of the disease to a given treatment. Once a proposed biomarker has been validated, it can be used to diagnose disease risk, presence of disease in an individual, or to tailor treatments for the disease in an individual (e.g., choices of drug treatment or administration regimes). In evaluating potential drug therapies, a biomarker may be used as a surrogate for a natural endpoint such as survival or irreversible morbidity. If a treatment alters the biomarker, which has a direct connection to improved health, the biomarker serves as a "surrogate endpoint" for evaluating clinical benefit.

As used herein, the term "assay element" refers to any of a number of different elements for use in an array of the invention. Exemplary assay elements include, but are not limited to, capture elements and control elements.

The term "capture element" refers to a molecule that is able to bind to a target analyte. Examples of useful capture elements include proteins, protein fragments, binding proteins, binding protein fragments, antibodies (polyclonal, monoclonal, or chimeric), antibody fragments, antibody heavy chains, antibody light chains, single chain antibodies, single-domain antibodies (a VHH for example), Fab antibody fragments, Fc antibody fragments, Fv antibody fragments, F(ab')2 antibody fragments, Fab' antibody fragments, single-chain Fv (scFv) antibody fragments, antibody binding domains, antigens, antigenic determinants, epitopes, haptens, immunogens, immunogen fragments, binding domains; a metal ion, a metal ion-coated molecule, biotin, avidins, streptavidins; substrates, enzymes, abzymes, co-factors, receptors, receptor fragments, receptor subunits, receptor subunit fragments, ligands, inhibitors, hormones, binding sites, lectins, polyhistidines, coupling domains, and oligonucleotides. Useful capture elements will correspond to and be able to bind a specific target analyte, such as a molecule or class of molecules that are present in a sample to be tested.

Equally, the term "control capture element" refers to a capture element that functions as a control, either a negative control that should not bind any analyte or a positive control that will bind a non-target analyte.

The term "control element" refers to an element that is used to provide information on the function of the assay, for example binding specificity, the level of non-specific background binding, the degree of binding cross-reactivity, and the performance of assay reagents and the detection system. Preferred controls useful herein include at least one negative control to monitor background signal, at least one negative control to monitor assay specificity, at least one positive colourimetric control, and at least one positive control to monitor assay performance.

The term "control to monitor assay performance" refers to an element that forms one part of a complementary binding interaction during an assay and is intended to provide information on the accuracy of the assay result. In one embodiment the positive control to monitor assay performance comprises one binding partner of a complementary binding pair, where the other binding partner is a sample component or an assay reagent. The assay performance control is preferably selected from a target analyte, a binding partner corresponding to and able to bind a non-target analyte that will be present in the sample, a binding partner corresponding to and able to bind an assay reagent, and a colourimetric enzyme label, or any combination of any two or more thereof. An example of a binding partner corresponding to and able to bind a non-target analyte that will be present in the sample is an anti-Ig antibody that will bind an immunoglobulin present in a serum sample, therefore confirming a sample has been added. An example of a binding partner corresponding to and able to bind an assay reagent is an anti-Ig antibody that will bind a secondary immunoglobulin that is used to process the assay, such as biotinylated anti-target analyte antibody. Another example of a binding partner corresponding to and able to bind an assay reagent is a biotinylated antibody that will bind a streptavidin-peroxidase conjugate that is used to process the assay.

The term "control to monitor assay specificity" refers to an element that is closely related to at least one binding partner of a complementary binding pair present in the assay and is intended to provide information of the specificity of the complementary binding. This control is a negative control that is not expected to generate a detectable result during normal assay processing. For example, in an antibody array for antigen detection, the assay specificity control would comprise an antibody that should not bind any antigen in the sample. Alternatively, in an antigen array for antibody detection, the assay specificity control would comprise an antigen that should not bind any antibody in the sample.

The term "fiduciary marker" refers to a coloured marker or label that will always be detectable on the membrane, preferably irrespective of the performance of the assay or processing of the membrane. The fiduciary marker acts therefore as a "true" positive control.

The term "microporous membrane" refers to a membrane with protein binding characteristics and a narrow pore-size distribution. In one embodiment the porosity of the membrane may determine the exposure time of reagents with membrane bound components by controlling the flow rate through the membrane. Microporous membranes for use in the present invention comprise nitrocellulose, nylon, polyvinylidene difluoride, polyester, polystyrene, polyethersulfone, cellulose acetate, mixed cellulose esters and polycarbonate.

The term "negative control" refers to an element comprising print buffer or an unrelated protein to which no complementary binding partner is intended to be present in the assay. Any detectable signal from the negative control can be used to determine the background threshold of the assay and the accuracy of any positive results. In one embodiment the negative control to monitor background signal is print buffer. The print buffer is a solution used to carry and print the capture elements and control elements onto the membrane and may comprise buffered saline, glycerol and a surfactant, preferably a polysorbate surfactant such as Tween 20. The blocking solution is used to reduce non-specific protein biding to the membrane surface and preferably comprises skim milk, casein, bovine serum albumin, gelatins from fish, pigs or other species, dextran or any mixture of any two or more thereof, preferably in a solution of phosphate buffered saline and a surfactant such as Tween 20.

The term "positive colourimetric control" as used herein refers to an enzyme or enzyme conjugate that provides a detectable signal upon addition of the enzyme substrate.

The term "printing" as used herein refers to the placement of the assay elements (control and capture elements) on the membrane surface, with or without an adapter molecule between the membrane and the element. Preferably the assay elements bind to the membrane by covalent or non-covalent interaction. One of skill in the art will recognize that methods of placing assay elements on the membrane include printing, spotting or other techniques known in the art. For purposes of the present application, the term "printing" can be used to include any of the methods for placing the assay elements on the membrane.

The terms "sample" and "specimen" as used herein are used in their broadest sense to include any composition that is obtained and/or derived from biological or environmental source, as well as sampling devices (e.g., swabs) which are brought into contact with biological or environmental samples. "Biological samples" include those obtained from an animal (including humans, domestic animals, as well as feral or wild animals, such as ungulates, bear, fish, lagamorphs, rodents, etc.), body fluids such as urine, blood, plasma, fecal matter, milk, nipple exudate, cerebrospinal fluid (CSF), semen, sputum, and saliva, as well as solid tissue. Biological samples also include a cell (such as cell lines, cells isolated from tissue whether or not the isolated cells are cultured after isolation from tissue, fixed cells such as cells fixed for histological and/or immunohistochemical analysis), tissue (such as biopsy material), cell extract, tissue extract, and nucleic acid (e.g., DNA and RNA) isolated from a cell and/or tissue, and the like. Also included are materials obtained from food products and food ingredients such as dairy items, vegetables, meat, meat by-products, and waste. "Environmental samples" include environmental material such as surface matter, soil, water, and industrial materials, as well as material obtained from food and dairy processing instruments, apparatus, equipment, disposable, and non-disposable items. In one embodiment, the biological sample is a cell, tissue, and or fluid obtained from a mammal, including from the upper respiratory tissues (such as nasopharyngeal wash, nasopharyngeal aspirate, nasopharyngeal swab, and oropharyngeal swab), from the lower respiratory tissues (such as bronchiolar lavage, tracheal aspirate, pleural tap, sputum), blood, plasma, serum, stool, milk, nipple exudate, and tissue from any organ such as, without limitation, lung, heart, spleen, liver, brain, kidney, and adrenal glands. These examples are illustrative, and are not to be construed as limiting the sample types applicable to the present invention.

The term "antibody" as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains (see Huse et al., *Science* 246:1275-1281, 1989, which is incorporated herein by reference). These and other methods of making, for example, chimeric, humanized, CDR-grafted, single chain, and bifunctional antibodies are well known (Winter and Harris, *Immunol. Today* 14:243-246, 1993; Ward et al., *Nature* 341:544-546, 1989; Harlow and Lane, *Antibodies: A laboratory manual* (Cold Spring Harbor Laboratory Press, 1999); Hilyard et al., *Protein Engineering: A Practical Approach* (IRL Press 1992); Borrabeck, *Antibody Engineering*, 2d ed. (Oxford University Press 1995); each of which is incorporated herein by reference). In addition, modified or derivatized antibodies, or antigen binding fragments of antibodies, such as pegylated (polyethylene glycol modified) antibodies, can be useful for the present methods. As such, Fab, F(ab')$_2$, Fd and Fv fragments of an antibody that retain specific binding activity are included within the definition of an antibody.

The term "secondary antibody" refers to an antibody that will bind a target analyte and that is conjugated with either an adaptor molecule such as biotin or an enzyme label such as horseradish peroxidase (HRP). Antibody-adaptor conjugates are processed to give a detectable result by contacting the antibody-adaptor conjugate with an adaptor-enzyme conjugate and then the enzyme substrate; for example, antibody-biotin conjugates will bind streptavidin-HRP conjugates. Antibody-enzyme label conjugates include antibody-HRP conjugates. Use of secondary antibodies is discussed and exemplified below.

The term "binds specifically" or "specific binding activity" or the like, means that two molecules form a complex that is relatively stable under physiologic conditions. The term is also applicable where, e.g., an antigen-binding domain is specific for a particular epitope, which is carried by a number of antigens, in which case the antibody carrying the antigen-binding domain will be able to bind to the various antigens carrying the epitope. Specific binding is characterized by a high affinity and a low to moderate capacity. Typically, the binding is considered specific when the affinity constant is about $1\times10^{-6}$ M, generally at least about $1\times10^{-7}$ M, usually at least about $1\times10^{-8}$ M, and particularly at least about $1\times10^{-9}$ M or $1\times10^{-10}$ M or less.

Array Design

As described above, one aspect of the invention relates to a microporous membrane for detecting a plurality (i.e., a panel) of target analytes (e.g., biomarkers) in a sample, the membrane comprising an array that comprises at least one capture element and a plurality of control elements printed on the membrane surface, the at least one capture element corresponding to and being able to bind a target analyte. When optionally included, the plurality of control elements include:

a) at least one fiduciary marker,
    b) at least one negative control to monitor background signal,
    c) at least one negative control to monitor assay specificity,
    d) at least one positive colourimetric control, and
    e) at least one positive control to monitor assay performance or any combination thereof.

The choice of membrane is dependent on three main membrane characteristics: protein-binding capacity, porosity, and strength. The ability of the membrane to immobilize macromolecules, in particular proteins is crucial as the membrane serves as the solid phase used in the assay. However, this ability must be balanced with the availability of appropriate reagents (i.e., blockers) for blocking non-specific interactions on the membrane. Similarly, in a flow-through configuration the porosity of the membrane may determine the exposure time of reagents with membrane bound components by controlling their flow rate through the membrane. However, porosity must be balanced with the degree of array spot spreading during array manufacture, which can result in decreased signal intensity or cross contamination between adjacent spots. The strength of the membrane is important for the manufacture and eventual use of a device. A wide range of membranes are available with differing characteristics, allowing a particular membrane to be chosen depending on the requirements of an assay.

In preferred embodiments, microporous membranes for use in the present invention comprise nitrocellulose, nylon, polyvinylidene difluoride, polyester, polystyrene, polyethersulfone, cellulose acetate, mixed cellulose esters and polycarbonate.

While some membranes such as cellulose acetate may have insufficient binding capacities for diagnostic immunoassays, the characteristics of such membranes may be applicable for assays where lower levels of accuracy or sensitivity are sufficient.

The microporous membrane is preferably removably attachable to a bottomless microtiter plate. Accordingly, the membrane can be divided into individual microtiter wells that are separated from each other by a physical barrier, to prevent sample mixing between wells. Moreover, different assays can be conducted in separate wells, requiring smaller volumes of assay reagents.

Capture elements specific for a target analyte are used to detect the presence or absence of the analyte in a sample. A wide range of complementary binding or coupling partners are known, with the choice of capture elements determined by the analytes to be detected, the requirement for adapter molecules and the level of specificity required for the assay.

In one embodiment the target analyte is selected from a protein, a protein fragment, a peptide, a polypeptide, a polypeptide fragment, an antibody, an antibody fragment, an antibody binding domain, an antigen, an antigen fragment, an antigenic determinant, an epitope, a hapten, an immunogen, an immunogen fragment, a metal ion, a metal ion-coated molecule, biotin, avidin, streptavidin, an inhibitor, a co-factor, a substrate, an enzyme, a receptor, a receptor fragment, a receptor subunit, a receptor subunit fragment, a ligand, a receptor ligand, a receptor agonist, a receptor antagonist, a signalling molecule, a signalling protein, a signalling protein fragment, a growth factor, a growth factor fragment, a transcription factor, a transcription factor fragment, an inhibitor, a monosaccharide, an oligosaccharide, a polysaccharide, a glycoprotein, a lipid, a cell, a cell-surface protein, a cell-surface lipid, a cell-surface carbohydrate, a cell-surface glycoprotein, a cell extract, a virus, a virus coat protein, a hormone, a serum protein, a milk protein, an oligonucleotide, a macromolecule, a drug of abuse, or any combination of any two or more thereof.

In one embodiment the capture element is selected from a protein, a protein fragment, a binding protein, a binding protein fragment, an antibody, an antibody fragment, an antibody heavy chain, an antibody light chain, a single chain antibody, a single-domain antibody (a VHH for example), a Fab antibody fragment, an Fc antibody fragment, an Fv antibody fragment, a F(ab')2 antibody fragment, a Fab' antibody fragment, a single-chain Fv (scFv) antibody fragment, an antibody binding domain, an antigen, an antigenic determinant, an epitope, a hapten, an immunogen, an immunogen fragment, a binding domain; metal ion, or metal ion-coated molecule, biotin, avidin, streptavidin; a substrate, an enzyme, an abzyme, a co-factor, a receptor, a receptor fragment, a receptor subunit, a receptor subunit fragment, a ligand, an inhibitor, a hormone, a binding site, a lectin, a polyhistidine, a coupling domain, an oligonucleotide, or a combination of any two or more thereof.

In another embodiment, the complementary binding partners comprise antibody-antigen interactions or antibody-ligand interactions.

In another embodiment, the capture elements may comprise antibodies or fragments thereof that are immobilised on the membrane surface and are specific for different antigens or ligands that may be present in a sample.

In another embodiment, the capture elements may comprise antigens or ligands and the assay involves the detection of specific antibodies that may be present in a sample.

In further embodiments, the capture elements may comprise of a receptor or a subunit of a receptor that binds a specific ligand.

In one embodiment the target analyte is associated with an infectious disease, allergic disease, autoimmune disease, cardiac disease, cancer or graft versus host disease.

In one embodiment the target analyte is selected from the list comprising angiogenesis factors such as Ang-2, FGF basic, HB-EGF, HGF, KGF, PDGF-BB, TIMP-1, TIMP-2, TPO and VEGF; Biomarkers such as A-SAA, Acrp-30 (Adiponectin), AR (Amphiregulin), Apo A-1, Apo B-100, C-peptide, sCD14, sCD30 (TNFRSF8), CD40L, CRP (C-reactive protein), ErbB2, FasL, Fibrinogen, Fibronectin, IGFBP-1, IGFBP-3, Leptin, LIF, MPO (Myeloperoxidase), NT-proBNP, OPG (Osteoprotegrin), OPN (Osteopontin), PAI-1 Active, PAI-1 Total, PAPP-A, PlGF (Placental Growth Factor), Prolactin, RANK, RANKL, Resistin, Tissue Factor and TRAIL; Cell Adhesion Molecules such as E-Cadherin, E-Selectin, ICAM-1, L-Selectin, P-Selectin and VCAM-1, Chemokines such as ENA-78, Eotaxin, Eotaxin-2, Exodus-2, GROα, GROγ, HCC-4 (CCL-16), I-309, IP-10, ITAC, Lymphotactin, MCP-1, MCP-2, MCP-3, MCP-4, MDC, MIF, MIG, MIP-1α, MIP-1β, MIP-1δ, MIP-3α, MIP-3β, MIP-4 (PARC), MPIF-1, NAP-2, RANTES, SDF-1β and TARC; Cytokines such as GM-CSF, G-CSF, IFNα, IFNγ, IL-1α, IL-1β, IL-1ra, IL-2, IL-3, IL-4, IL-5, IL-6, IL-7, IL-8, IL-9, IL-10, IL-11, IL-12p40, IL-12p'70, IL-13, IL-15, IL-16, IL-17, IL-18 and TNFα; Cytokine receptors such as IL-2R, IL-2Rγ, IL-6R, TNF-RI and TNF-RII; Growth Factors such as, EGF, HGH, TGFα and TGFβ; Immunoglobulins such as IgA, IgD, IgE, IgG and IgM; Matrix Metalloproteinases such as MMP-1, MMP-2, MMP-3, MMP-7, MMP-8, MMP-9, MMP-10 and MMP-13; and Neurotrophic Factors such as β-NGF, BDNF, CNTF and NT3, or any combination of any two or more thereof.

In another embodiment the target analyte is an antigen from a family, genus, species, subtype or individual microorganism. Exemplary microorganisms include, but are not limited to, *Mycobacterium, Brucella, Bacillus, Treponema, Clostridium, Staphylococcus, Enterococcus, Streptococcus, Haemolyticus, Pseudomonas, Campylobacter, Enterobacter, Neisseria, Proteus, Salmonella, Simonsiella, Riemerella, Escherichia, Neisseria, Meningococcus, Moraxella, Kingella, Chromobacterium* and *Branhamella*, or from a virus such as adenovirus, influenza, cytomegalovirus, hepatitis, human immunodeficiency virus, avian influenza virus, respiratory syncytial virus, herpex simplex virus, parainfluenza virus, pestivirus, porcine parvovirus, peudorabies virus, rotavirus, calicivirus, canine distemper virus, or from other microorganisms such as *Leptospira, Toxoplasma, Trypanosoma,* or *Plasmodium*, or any combination of any two or more thereof.

Other exemplary target analytes include, but are not limited to, human chorionic gonadotropin, growth hormone, insulin, glucagon, adrenocorticotropic hormone, thyroid stimulating hormone, a-fetoprotein, human placental lactogen, leptin, inhibin A, activin A, pregnancy-associated plasma protein A, placenta growth factor, pregnancy-specific beta-1 glycoprotein; steroids such as testosterone, oestriol, cortisol, progesterone, corticosterone, aldosterone; thyroid hormones such as thyroxine, triiodothyronine; thyroid binding globulin (TBG); active peptides such as bradykinin, gastrin, angiotensin, thyroid hormone-releasing hormone, luteinising hormone-releasing hormone; physiologically active amines such as epinephrine, norepinephrine, histamine, serotonin; prostaglandins, such as PGF2a, PGE, thromboxanes and prostacyclins, or any combination of any two or more thereof.

In another embodiment the target analyte is an allergen. Exemplary allergens include, but are not limited to, indoor allergens such as Mites, Tyr. put, Lep. dest. or. mayrei, *Felis, Bos,* Albumine, Pen. cit., Pen. not., *Asp. fumigatus,* Alt. alt., *Malassezia furfur, Latex, Plodia, Blatella*; outdoor allergens such as *Betula, Juniperus, Phleum, Parietaria* and *judicea*; representative allergens from cats, dogs, mouse, rat, pig, a sheep, chicken, rabbit, a hamster, a horse and pigeon, food allergens such as celery, carrot, peanut, apple, shrimp and fish; venom allergens such as bee or wasp, auto-allergens such as liver membrane antigens, ssDNA antigens and antigens in or on skeleton muscle cells, and any combination of any two or more thereof.

In another embodiment, one or more capture agents are arranged to detect one or more (i.e., a panel) target analytes (i.e., biomarkers) that would be indicative of particular human conditions or diseases. Such tests could consist of any combination of the panels listed in Table 1, depending upon local requirements.

TABLE 1

| Human Condition/Disease Panels | |
| --- | --- |
| Infectious Disease Screening for Epidemiological Studies in Developing Nations | Human immunodeficiency virus (HIV)-1, HIV2, Hepatitis A virus, Hepatitis B virus, Hepatitis C virus, Herpes simplex virus (HSV)-1, HSV-2, *Treponema pallidum, Mycobacterium tuberculosis, Neisseria gonorrhoeae, Plasmodium falciparum.* |
| Upper Respiratory Viral Infections | Adenovirus, Cytomegalovirus (CMV), Influenza A, Influenza B, Parainfluenza 1, Parainfluenza 2, Parainfluenza 3 and Respiratory Syncytial Virus (RSV), Group A Streptococci. |
| Acute Lower Respiratory Infections | *Streptococcus pneumoniae, Haemophilus influenzae, Mycoplasma pneumoniae, Chlamydia pneumoniae, Moraxella catarrhalis,* C-reactive protein, procalcitonin. |
| Gastrointestinal Pathogen Panel | *Salmonella, Shigella, Campylobacter, Vibrio.* |
| Panel for Liver Viral Disease Testing | Hepatitis virus A, B, C, D, E and G surface and core antigens, anti-Hepatitis A, B, C, D, E and G serum antibodies. |
| Sexually Transmitted Disease Panel | Human immunodeficiency virus (HIV)-1, HIV2, *Treponema pallidum, Neisseria gonorrhoeae, Chlamydia trachomatis.* |
| Blood Borne Disease Panel | *Plasmodium falciparum* (malaria), *Trypanosoma cruzi* (Chagas disease), *Brucella* spp (Brucellosis), Human immunodeficiency virus (HIV)-1, HIV2, Hepatitis A virus, Hepatitis B virus. |
| ToRCH Panel | *Toxoplasma gondii,* Rubella virus, Cytomegalovirus and Herpes simplex virus1 and HSV2. |
| Biosecurity Panel | *Bacillus anthracis* (anthrax), *Clostridium botulinum* (botulism), *Clostridium perfringens, Yersinia pestis* (plague), *Coxiella burnetii* (Q fever), Staphylococcal enterotoxin B, *Vibrio cholerae* (Cholera). |
| Fertility Panel | Estradiol, follicle stimulating hormone, human chorionic gonadotrophin, lutenizing hormone, progesterone, prolactin, testosterone, parathyroid hormone. |
| Drugs of Abuse Panel | Acetaminophen, Amphetamines, Barbiturates, Cannabinoids, cocaine metabolites, methadone, opiates, salicylate and tricyclic anti-depressants. |
| Panel for Cardiovascular Disease Testing | Brain natriuretic pepetide (BNP), N-terminal proBNP (Nt-proBNP), creatine kinase (CK)-MB, myoglobin, cardiac Troponin I, cardiac Troponin T, High-sensitivity C-reactive protein. |
| Panel for Autoimmune Disease Testing | Rheumatoid factor, C-reactive protein, soluble human leukocyte antigen (HLA)-DR, antibodies against double stranded DNA, citrullinated peptides, small nuclear ribonucleoproteins, neutrophil cytoplasmc (ANCA) and nuclear antigens (ANA). |
| Panel for Measuring Hormone Levels | Insulin, Leptin, Thyroxin3 and 4 , Thyroid Stimulating Hormone (TSH), growth hormone, testosterone, estrogen, leutenizing hormone. |
| Panel for General Cancer Testing | Free and total Prostate specific antigen (PSA), Carcinoembryonic antigen (CEA), CA125, CA15-3, CA19-9, CA24-2, CA72-4, alpha fetoprotein (AFP). |

TABLE 1-continued

| Human Condition/Disease Panels | |
| --- | --- |
| Markers of Inflammation | Interleukin (IL)-1α and β, IL1 receptor antagonist, IL2, IL4, IL6, IL8, IL10, IL12, IL13, IFNγ, TNFα, MIP1α and β, MCP1, RANTES, soluble VCAM, C- reactive protein, soluble TNFα receptor I and II. |
| Allergen Panel to Screen for Serum IgE Binding | Allergens obtained by recombinant methods or derived from dust mites, grass and tree pollen, animal dander, moulds, insect venoms and foods such as soy protein, milk proteins, proteins derived from varieties of nuts, cereals and legumes, proteins from seafood such as shrimp, abalone and lobsters. |

In another embodiment, one or more capture agents are arranged to detect one or more (i.e., a panel) target analytes (i.e., biomarkers) that would be useful in determining treatment efficacy for the indicated diseases. Such tests could consist of any combination of the panels listed in Table 2, depending upon local requirements.

TABLE 2

| Panels to Determine Efficacy of Treatments | |
| --- | --- |
| Autoimmune Diseases | Cytokines and chemokines including CTLA4, tumor necrosis factor alpha (TNFα), bLyS (BAFF), interferon gamma (IFNγ), eotaxin, CXCL10 or IP10, osteopontin, osteoprotegerin and RANKL. Other biomolecules such as pyridinoline, deoxypyridinoline, cartilage oligomeric matrix protein. Antibodies against double stranded DNA, small nuclear ribonucleoproteins, nuclear proteins such as Sjogren's Syndrome antigen (SS)-A and SS-B, nuclear antigen, Sm antigen, ribosomal P proteins, cardiolipin and topoisomerase I. Antibodies against therapeutic proteins such as abatacept (an immunoglobulin fused to the ectodomain of CTLA4), rituximab (a chimeric anti-CD20 antibody), tocilzumab (anti-IL6 receptor antibody), etanercept (recombinant soluble human TNFα fused to IgG), infliximab (a chimeric anti-TNFα antibody), adalimumab (a humanized anti-TNFα antibody), anakinra (a human IL6 receptor antagonist protein) and others. |
| Cancer | Human chorionic gonadotrophin, Tyrosinase, HMGB1, S100-beta, melanoma inhibitory activity (MIA), soluble HLA-DR, matrix metalloproteinases (MMP)) such as MMP-1 and MMP-9, cytokines including Interleukin (IL)-6, IL8 and IL10, high molecular weight melanoma-associated antigen (HMW- MAA), haptoglobin, osteopontin, moiesin, transferrin, FK506, haptoglobin precursor protein, progesterone receptor, estrogen receptor, serine protease urokinase-type plasminogen activator, plasminogen activator inhibitor Type I, human papilloma virus, Epstein-Barr virus, Glutathione S-transferase PI. Antibodies against therapeutic proteins such as rituximab (a chimeric anti-CD20 antibody), cetuximab (a chimeric anti-EGF antibody), trastuzumab (humanized anti-Her2/neu antibody), tositumomab (mouse monoclonal anti-CD20 antibody), gemtuzumab (humanized anti-CD33 antibody), bevacimumab (a humanized anti-VEGF antibody), alemtuzumab (a humanized anti-CD52 antibody) and Ibritumomab tiuxetan (mouse anti-CD20 antibody). |
| Cardiovascular Diseases and Stroke Risk Assessment | Interleukin (IL)-1, IL-6, IL-10, ischemia- modified albumin, monocyte chemoattractant protein (MCP)-1, plasminogen activator-1, TNFα, von Willebrand factor, soluble CD40 ligand, myeloperoxidase, placental growth |

TABLE 2-continued

Panels to Determine Efficacy of Treatments factor, fibrinogen, and heart-type fatty acid binding protein (H-FABP), matrix metalloproteinase (MMP)-9, B-type neurotrophic growth factor (BNGF), serum amyloid A, fibrinogen, sICAM and S-100b.

In another embodiment, one or more capture agents are arranged to detect one or more (i.e., a panel) target analytes (i.e., biomarkers) that would be useful in animal testing. Such tests could consist of any combination of the panels listed in Table 3, depending upon local requirements.

TABLE 3

Animal Testing Panels

| | |
|---|---|
| Avian | Avian influenza virus, Avian pneumovirus, Avian reovirus, avian rhinotracheitis virus, Chicken anemia virus. |
| Bovine | Bovine Adenovirus, Bovine Coronavirus, *Leptospira* spp, Bovine leukosis Virus, Bovine respiratory syncytial virus, bovine spongiform encephalopathy, bovine viral diarrhoea virus, *Brucella abortus*, *Neospora caninum*, *Mycoplasma bovis*, Bovine babesiosis, Rotavirus, contagious bovine pleuropneumonia, bovine Herpes Virus Type I and II, bovine parainfluenza 3. |
| Canine | Canine distemper virus, canine coronavirus, canine herpes virus, canine parvovirus, *Borrelia burgdorferii*, *Rickettsia rickettsii*, *Ehrlichia canis*, *Rickettsia conori*, canine rheumatoid factor, dog erythrocyte antigen, canine Hepatitis virus 1 and 2, canine parainfluenza 1, *Borrelia afzelii*, *Leishmania donovani*, *Ehrlichia equi*, *Rickettsia conorii*. |
| Equine | Equine arteritis virus, equine infectious anemia virus, equine herpesvirus Type I, equine adenovirus, equine influenza virus, *Babesia equi*, *Babesia caballi*, *Borrelia burgdorferii*, *Borrelia afzelii*, *Ehrlichia equi*, *Leishmania donovani*. |
| Feline | Feline coronavirus, feline calicivirus, feline leukemia virus, feline herpesvirus, Feline immunodeficiency virus, feline infectious peritonitis virus, feline panleukopaenia virus, feline viral rhinotracheitis virus, Feline Enteric Corona Virus. |
| Porcine Pathogens | Porcine influenza A virus, porcine parvovirus, porcine reproductive and respiratory syndrome virus, Pseudorabies virus, porcine rotavirus, porcine *Brucella suis*, transmissible gastroenteritis (TGE) virus, classical swine fever virus, porcine respiratory coronavirus. |
| Ovine Pathogens | Ovine Herpes virus, *Brucella ovis*, pseudorabies virus (Aujesky's). |
| Protein and Endocrine Panel for All Species | Estrone sulfate, progesterone, growth hormone, serum cortisol, testosterone, thyroxine (T)-3, T-4, Serum albumin, serum globulin, insulin, parathyroid hormone, thyroid stimulating hormone, leutenizing hormone. |
| Panel of Pathogens to Test for Export | Bovine viral diarrhoea virus, enzootic bovine leucosis virus, bovine Herpes Virus Type I, Maedi visna virus, *Brucella ovis*, *Mycobacterium paratuberculosis* (Johne's disease), *Campylobacter fetus*, *Trichomonas foetus*, *Leptospira* spp, *Streptococcus equi*, Infectious bovine rhinotracheitis virus. |
| Panel for Mastitis Testing of Cattle | *Streptococcus agalactiae*, *Streptococcus uberis*, *Staphylococcus aureus*, *Mycoplasma* spp, *Eschericia coli*, *Klebsiella* spp, *Pseudomonas* spp, *Prototheca* spp., Haptoglobin, serum amyloid A, immunoglobulins, lactoferrin, serum albumin. |

TABLE 3-continued

Animal Testing Panels

| | |
|---|---|
| Markers of Inflammation | Interleukin (IL)-1α and β, IL1 receptor antagonist, IL2, IL4, IL6, IL8, IL10, IL12, IL13, IFNγ, TNFα, MIP1α and β, MCP1, RANTES, soluble VCAM, C-reactive protein, soluble TNFα receptor I and II. |

After array manufacture and prior to sample addition, all available protein-binding sites on the membrane surface are blocked by addition and incubation with one or a combination of reagents. These reagents are called "Blockers" and serve to decrease or at best eliminate non-specific protein binding from the sample on the membrane surface thereby decreasing overall background signal. This increases the ratio of signal to noise, thereby increasing the overall sensitivity of the assay. Blockers play no active part in the subsequent reactions between the sample and other assay reagents and the immobilized proteins on the membrane. Exemplary blockers include, but are not limited to, bovine serum albumin, casein, non-fat dry milk, gelatin derived from fish, pigs and other sources, dextran, serum derived from sources other than the sample being analysed such as from steelhead salmon, guinea pigs, hamsters, rabbit and other sources, polyethylene glycol, polyvinyl pyrrollidone, and commercial preparations including HeteroBlock (Omega Biologicals, Bozeman, Mont.), SuperBlock, StartingBlock, SEA BLOCK (Pierce, Rockford, Ill.). Typically, blockers are made up in buffer solutions such as, for example, phosphate buffer, phosphate buffered saline, Tris buffer, acetate buffer and others. The blockers may also be supplemented with detergents such as, for example, Tween 20, Tween 80, Nonidet P40, sodium dodecyl sulfate and others.

The membrane of the invention comprises at least one fiduciary marker that will always be detectable on the membrane, preferably detectable irrespective of the performance of the assay or processing of the membrane.

In preferred embodiments the fiduciary marker is a dye, dye-conjugated protein or a chromogenic protein such as haemoglobin.

The use of at least one fiduciary marker will obviate the necessity of this element being detected based on successful array processing, in comparison to the positive colourimetric controls. The fiduciary marker is therefore a "true" positive control that would always be detectable regardless of array processing, and can be used to orient and help to grid the array.

The membrane of the invention also comprises at least one control to monitor assay specificity. The control is intended to provide information of the specificity of binding between the capture element and the target analyte, or between the binding partners of the assay detection steps.

In one embodiment the assay specificity control comprises one or more antibody isotypes, a corresponding antibody or antibody isotype from a different animal species or a closely related ligand. For example, in human antibody arrays, human IgM and anti-human IgM can be used as controls to monitor assay specificity.

The membrane of the invention also comprises at least one control to monitor assay performance. The control is intended to provide information of the efficiency of the complementary binding interactions or the quality or performance of the reagents used.

In one embodiment the assay performance control comprises one binding partner of a complementary binding pair, wherein the other binding partner is an assay reagent. The assay performance control is preferably selected from the list comprising the target analyte, a non-specific binding partner or a colourimetric enzyme label.

In one embodiment the positive colourimetric control is an enzyme label conjugate capable of reacting with a colourimetric substrate, comprising an enzyme selected from the list comprising horseradish peroxidase, alkaline phosphatases, β-D-galactosidase or glucose oxidase.

The identity of the assay controls will be dependent on the type of array, the identity of the target analyte, and the type of sample to be analyzed.

For example, either anti-human IgG-HRP or anti-mouse IgG-HRP may be used in arrays printed with antigens and antibodies, respectively. The final detection antibody in antigen arrays will often be anti-human IgG-HRP, while for antibody arrays it will often be a biotinylated mouse IgG. These controls can provide a positive control in addition to providing information on the performance or quality of the HRP substrate.

Mouse IgG, human IgG and anti-human IgG present on antigen or antibody arrays can act either as positive or negative controls depending on the array format, in addition to providing information of assay specificity. For example, mouse IgG should provide the positive signal in antibody arrays, while the latter two should provide a positive signal in antigen arrays. In allergen arrays, human IgM and anti-human IgM may be replaced as controls with human IgE and anti-human IgE. These controls can also serve as controls for overall assay performance.

In preferred embodiments the elements on the array are printed in discrete areas of between 100 µm to 500 µm in diameter. More preferably, the discrete areas are between 350 µm to 400 µm in diameter.

In preferred embodiments, the discrete areas of the array are printed in a 5×5 grid. Preferably the array comprises up to nine control elements and two replicates of each of eight different capture elements.

In preferred embodiments the capture elements are printed in two or more replicates of four different capture elements and multiples thereof.

Detection of Target Analytes

The assay techniques used in conjunction with the membranes of the present invention include any of a number of well known colourimetric enzyme-linked assays. Examples of such systems are well known in the art. The assay techniques are based upon the formation of a complex between a complementary binding pair, followed by detection with a colourimetric detection system comprising an enzyme-conjugate label and a colourimetric substrate. In the present invention, the solid phase carrier or substrate is a microporous membrane. The detection system will be described with reference to enzyme-linked immunosorbent assays (ELISA), though a skilled person would appreciate that such techniques are not restricted to the use of antibodies but are equally applicable to any colourimetric assay.

FIG. 1 shows a schematic representation of assay formats and sample processing flow. Panel (A) shows the processing steps of an antibody array for detection of antigens or ligands from biological test samples. Panel (B) shows the processing of an antigen or ligand array for detection of antibodies in biological test samples. Panel (C) shows the general sample processing flow in which each of the reagents described below and in the Examples are added to the array printed according to Example 1.

Figure 2:
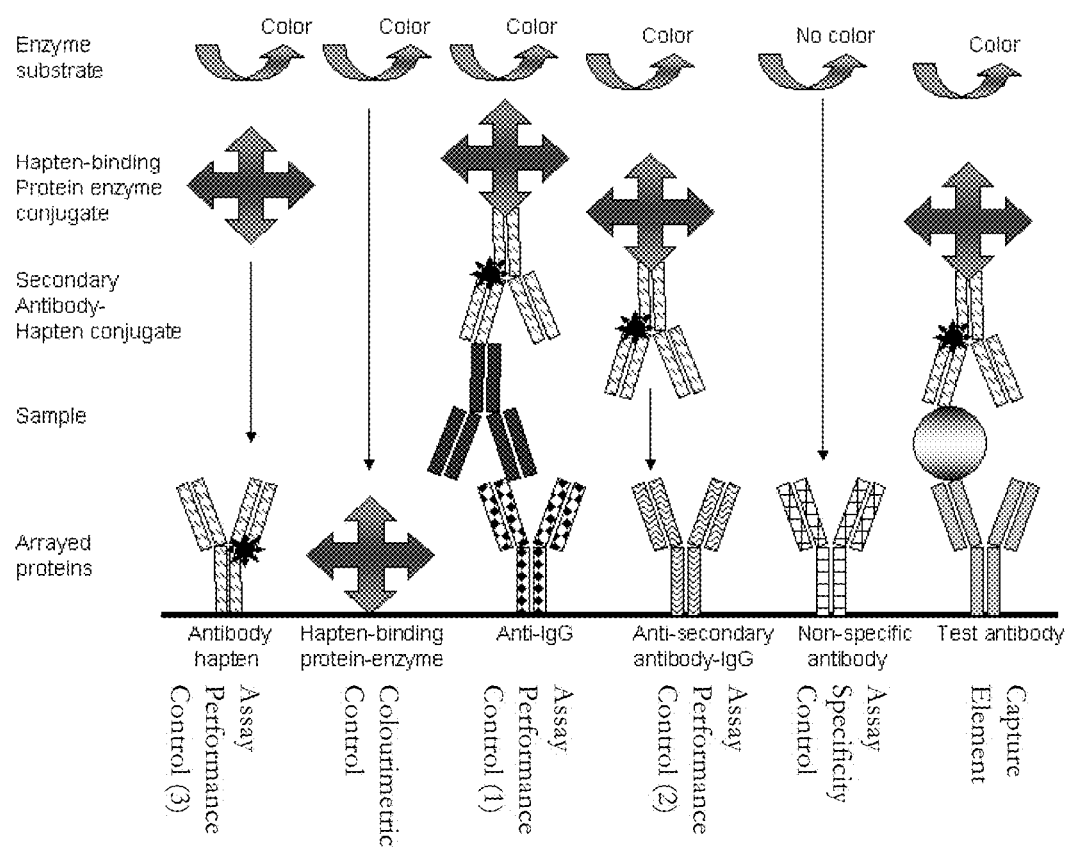
FIG. 2 is a pictorial diagram summarizing the function and processing of the controls spots present in an array printed on an assay membrane of the invention.

FIG. 2 shows a schematic representation of function of control elements and their binding to various reagents added during processing of an antibody assay for antigen detection. The addition of various reagents is shown on the left of the figure with sequential additions being made from bottom to top. Color is developed only if the appropriate functional reagent binds to the control element.

In one embodiment the ELISA is in the "sandwich" assay format. In this format the target analyte to be measured is bound between two antibodies—the capture antibody and the detection antibody. In another embodiment the ELISA is a non-competitive assay, in which an antibody binds to the capture antigen and the amount of bound antibody is determined by a secondary detection antibody.

In another embodiment the ELISA is a competitive assay, where a labelled antigen is used instead of a labelled antibody. Unlabelled antigen and the labelled antigen compete for binding to the capture antibody and the amount of target analyte bound can be determined by the proportion of labelled antigen detected.

Either monoclonal or polyclonal antibodies may be used as the capture and detection antibodies in sandwich ELISA systems. Monoclonal antibodies have an inherent mono-specificity toward a single epitope that allows fine detection and quantitation of small differences in antigen. A polyclonal antibody can also be used as the capture antibody to bind as much of the antigen as possible, followed by the use of a monoclonal antibody as the detecting antibody in the sandwich assay to provide improved specificity. A monoclonal antibody can also be used as the capture antibody to provide specific analyte capture, followed by the use of a polyclonal antibody as the detecting antibody in the sandwich assay.

An important consideration in designing an array is that the capture and detection antibodies of each binding pair must recognise two non-overlapping epitopes so that when the antigen binds to the capture antibody, the epitope recognised by the detection antibody must not be obscured or altered. A large number of complementary binding pairs have already been developed for ELISA and can be used in the present invention.

For multiplexed assays it is also important that there is no overlap between each of the binding pairs to eliminate crossreactivity. A number of multiplexed ELISAs have been developed and it is anticipated other combinations of binding pairs could be configured through testing.

In one embodiment the enzyme-conjugate label comprising an enzyme selected from the list comprising horseradish peroxidase, alkaline phosphatase, β-D-galactosidase or glucose oxidase.

In one embodiment the enzyme label may be conjugated directly to a primary antibody or introduced through a secondary antibody that recognises the primary antibody. It may also be conjugated to a protein such as streptavidin if the primary antibody is biotin labelled.

In one embodiment the assay detection system comprises a detection colourimetric substrate selected from the list comprising 3,3',5,5'-tetramethylbenzidine, diaminobenzidine, metal-enhanced diaminobenzidine, 4-chloro-1-naphthol, colloidal gold, nitro-blue tetrazolium chloride, 5-bromo-4-chloro-3'-indolylphosphate p-toluidine salt and naphthol AS-MX phosphate+Fast Red TR Salt.

In preferred embodiments the colourimetric reaction can be detected and optionally quantified and analysed using an image capture device such as a digital camera or a desktop scanner attached to a computer. Known methods for image analysis may be used. For example, the density values of known standard elements can be used to generate standard curves. Density values for unknown analytes can be analysed using the standard curve for each analyte to calculate actual concentrations. Values for each analyte can be identified based on the spotting position of each capture element within the array.

Membranes of the present invention are particularly amenable to use in kits for the detection of target analytes. Such kits may comprise the membranes together with instructions and any assay consumables required. Different kits are envisaged for different target analytes and types of array. Accordingly, in one aspect the invention relates to a kit comprising a membrane of the invention and optionally, one or more processing reagents. For example, a kit of the invention optionally includes one or more of, or any combination of any two or more of:

a) a background reducing reagent (otherwise known as a blocking solution),
b) a wash solution,
c) one or more antibodies (including antibody-binding protein conjugates or antibody-enzyme label conjugates or both) for detection of antigens, ligands or antibodies bound to the capture elements or for detection of the positive controls,
d) a colourimetric detection system,
e) software for determination of signal intensity at each spot and analysis of results, and
f) a protocol for measuring the presence of analytes in samples.

In another aspect the invention also relates to a method of processing a membrane of the invention. Such a method comprises:

a) providing a membrane of the invention as described above,
b) adding at least one sample to the membrane, and
c) processing the membrane such that a detectable result is given by two or more of:
   i) at least one fiduciary marker,
   ii) at least one positive colourimetric control, and
   iii) at least one positive control to monitor assay performance.

In one embodiment the step of processing the membrane comprises a blocking step during which available protein-binding sites on the membrane are blocked with a blocker, an optional wash step, contacting the membrane with the sample containing the one or more analytes to be measured, a wash step to remove non-bound material from the membrane, contacting the membrane with one or more secondary antibodies that correspond to and will bind one or more target analytes and non-target analyte that is bound to an assay performance control, a wash step, and contacting the membrane with one or both of an enzyme conjugate or an enzyme substrate to generate a detectable result. Examples of processing a membrane of the invention are described below.

In another embodiment, the microporous membranes of the invention can be used for the simultaneous detection of at least one target analyte in a sample, and preferably a plurality of different target analytes in a sample, and have utility in diagnostic and screening assays.

Thus, the microporous membranes of the invention provide the advantage that they can be adapted to high throughput (or ultra high throughput) analysis and, therefore, any number of samples (e.g., 96, 1024, 10,000, 100,000, or more) can be examined in parallel, depending on the particular support used. A particular advantage of adapting the microporous membranes to high throughput analysis is that an automated system can be used for adding or removing reagents from one or more of the samples at various times, for adding different reagents to particular samples, or for subjecting the samples to various heating cycles.

For example, the automated system may consist of one or more temperature-controlled chambers and one or more robotic arms mounted on a deck that has platforms configured to hold 96-well plates. The movement of the robotic arms and the temperature in the chambers are controlled by a central computer unit. The array plates are stacked on the deck of the instrument. In one embodiment, the plates containing samples to be analysed are stacked in a chamber with temperature of 4° C. One robotic arm then sequentially transfers each individual array plate on one platform while the other arm sequentially transfers each individual sample plate on the second platform. A nozzle containing 96 disposable tips then aspirates a predetermined volume of sample from each well of the sample plate and transfers the sample to the corresponding wells of the array plate. The array plate containing the sample is then transferred to a chamber with temperature of 37° C. This process is repeated until sample has been added to all the array plates stacked on the deck. The array plates are incubated for a predetermined time followed by transfer of each plate to the platform for addition of wash buffer with the nozzle containing 96 disposable tips. The wash buffer is aspirated after a predetermined time and this wash process is repeated multiple (i.e., two or more) times. Each array plate then receives the secondary antibody followed by transfer to a chamber with temperature of 37° C. The array plates are incubated for a predetermined time followed by transfer of each plate to the platform for addition of wash buffer with the nozzle containing 96 disposable tips. The wash buffer is aspirated after a predetermined time and this wash process is repeated multiple (i.e., two or more) times. Each array plate then receives the detection reagent followed by incubation for a predetermined time followed by transfer of each plate to the platform for addition of wash buffer with the nozzle containing 96 disposable tips. The wash buffer is aspirated after a predetermined time and the plate transferred to the 37° C. chamber for drying. The plates are transferred back to the deck after a predetermined period and manually processed for analyses of data.

In addition to the convenience of examining multiple test agents and/or samples at the same time, such high throughput assays provide a means for examining duplicate, triplicate, or more aliquots of a single sample, thus increasing the validity of the results obtained, and for examining control samples under the same conditions as the test samples, thus providing an internal standard for comparing results from different assays.

Various aspects of the invention will now be illustrated in non-limiting ways by reference to the following examples.

EXAMPLES

Example 1

General Procedures for Array Manufacture

Membranes or films attached to a bottomless 96-well polystyrene plate (such as nylon, Nalge Nunc International, USA,) were used for printing microarrays. Various methods may be used to attach the membranes to the 96-well bottomless plates. In this example, a rubber sheet with dimensions of 128 mm length and 86 mm and 1 mm thickness was used. 96 round holes were stamped on the sheet with a diameter of 6.35 mm and a center to center distance of 9 mm. The sheet was then coated with adhesive on both sides and glued to one side of the 96-well bottomless plate such that the second adhesive layer was still available for binding to a membrane. A nylon membrane was then cut to the dimensions of 128 mm length and 86 mm width and attached to the other side of the rubber sheet to create a gasket that creates leak proof wells.

Another method for attaching the membranes to the 96-well bottomless plates involves use of an adhesive that is applied to one side of the plate. Thereafter, a nylon membrane cut to the dimensions of 128 mm length and 86 mm width is attached using pressure such that there is no leakage between the wells.

Microarrays were printed by mixing proteins in a print buffer solution containing phosphate buffered saline, glycerol and Tween 20 to give a final concentration of 10% glycerol and 0.005% Tween 20.

Arrays were printed by using a benchtop contact microarrayer (LabNext Inc, USA) using quill pins designed to give uniform spots with an average diameter of 350 µm (Chip-Maker II, Telechem International Inc, USA). Arrays were printed at ambient temperature and humidity of 60% (±10%).

Up to ninety-six replicate arrays were printed on the membrane. Each array had up to 25 spots printed in 5×5 grids (Number of Columns×Number of Rows). Arrays with less than 25 spots were printed such that they contained 5, 10, 15 or 20 spots in patterns of 5×1, 5×, 5×3 and 5×4 spots.

Each array had a series of control spots that were printed in Column 1 and Row 5. These control spots included a fiduciary marker (a dye-conjugated protein such as BlueRanger Prestained Protein Molecular Weight Marker, Pierce Biotechnology Inc, USA, Catalog Number 26681), negative control (phosphate buffered saline containing 20% glycerol and 0.005% Tween 20 and a non-specific antibody), positive controls (enzyme-conjugated protein such as streptavidin conjugated horseradish peroxidase, Pierce, Catalog Number 21126) and sample specific controls to monitor the overall performance of the assay.

Test proteins were printed at concentrations ranging from 0.05 mg/ml to 1.0 mg/ml, usually 0.5 mg/ml, determined by the binding affinity of the specific protein to the analyte being measured.

After printing the arrays were kept at 4° C. for at least 8 hours before use.

Example 2

General Procedure for Array Processing and Analysis

The arrays were incubated at 37° C. for 60 min after adding 100 l of Blocker [1% casein (Vector Labs, USA) in phosphate buffered saline containing 0.1% Tween 20 (PBS-T)] to each well. The Blocker was then aspirated off.

Samples containing analytes were added by diluting in Blocker at a volume of 50 µl in each well and the membrane incubated at 37° C. for 60 min. The membrane was washed 3× with PBS-T to remove excess non-bound analytes.

For antibody arrays (for antigen detection), adapter-conjugated detection antibodies were added to the wells at concentrations either recommended by the manufacturer or empirically determined by experimentation. Examples of adapter-conjugated antibodies include hapten-conjugated antibodies such as biotin-conjugated antibodies. The membrane was incubated at 37° C. for 60 min and washed 3× with PBS-T. The membrane was then incubated with an anti-adapter antibody (such as an anti-biotin antibody) conjugated to an enzyme or an adapter-conjugated enzyme (such as a streptavidin-conjugated enzyme) for 37° C. for 60 min. An example of an enzyme is horseradish peroxidase. The membrane was washed 3× with PBS-T.

Alternately, for antigen arrays (for antibody detection), after washing excess analytes, the membrane was incubated with anti-immunoglobulin antibodies conjugated with an enzyme such as horseradish peroxidase. The membrane was incubated for 37° C. for 60 min. The membrane was washed 3× with PBS-T.

In either case, the bound enzyme was detected and measured using an enzyme substrate that results in a colored precipitate deposited on the protein spot. An example of a substrate used is metal enhanced diaminobenzidine (Pierce, USA) that gives a brown precipitate with horseradish peroxidase. Alternatively the bound anti-analyte antibodies can be detected using a second antibody or adapter such as streptavidin conjugated to colloidal gold.

The membrane was dried for 60 min at ambient temperature and scanned at 600 dpi resolution or photographed using a digital camera with a resolution of at least 4 megapixels and the image saved in the TIFF format.

The color intensity at each spot was determined using gridding software that placed grids on all the arrays using the fiduciary marker to align the grid at the appropriate position. The intensity values were obtained in a Microsoft Excel™ spreadsheet file, which can then be used for analysis of results.

Example 3

Antibody Arrays

Arrays for detection of antigens such as protein markers of autoimmune diseases, cardiovascular diseases, cancer and infectious agents, or ligands such as growth factors, hormones, cytokines and chemokines are created by printing panels of antibodies as capture elements for specific capture of the antigen. A series of control antibodies and control proteins are also printed. These controls serve a variety of functions including controls for monitoring assay performance including performance of individual reagents, controls for monitoring the specificity of the capture antibodies and fiduciary markers for gridding the arrays after sample processing for determination of signal intensity at each spot in the array. Table 4 summarises the reagents that may be used to print and process antibody arrays. The assay performance control numbering relates to the numbering in FIG. 2.

TABLE 4

Antibody Array Reagents

| Reagent | Function | Example | Comments |
| --- | --- | --- | --- |
| Protein or Antibody with a | Fiduciary marker to enable the gridding software to | BlueRanger dye conjugated | The fiduciary marker will always be detectable. |

TABLE 4-continued

Antibody Array Reagents

| Reagent | Function | Example | Comments |
|---|---|---|---|
| Chromogenic Dye | locate and place grids on each spot of the array | protein marker | |
| Print Buffer | Negative control for determining the background signal in the array | | |
| Antibody Conjugated to a Hapten (e.g. Biotin) | Control to monitor the function of enzyme-conjugated Streptavidin or any other biotin-binding protein(BP) (assay performance (3)) | Anti-mouse IgG conjugated to biotin | |
| Hapten Binding Protein- Enzyme Conjugate | Positive colourimetric control to monitor the performance of the enzyme substrate | Streptavidin-horseradish peroxidase | |
| Anti-IgG Antibody | Control to demonstrate the addition of sample (assay performance (1)) | | Addition of serum will result in binding of serum IgG to this spot; If non-human sample is to be tested the antibody will be replaced with one appropriate for capture of IgG from the species being tested |
| IgG for Capture of Detection Antibodies Conjugated to Hapten | Control to demonstrate the addition of secondary detection antibody mix (assay performance (2)) | Anti-mouse IgG | The secondary biotinylated monoclonal antibodies will bind to the anti-mouse IgG |
| Non-Specific Antibody | Negative control for determining antigen capture specificity (assay specificity) | Hamster IgG | IgG from a species not represented in the array panel and detection reagents |
| Panel of Test Antibodies for Capture of Antigens or Ligands | Diagnostic tests for disease or wellness markers (capture elements) | Anti-cytokine antibody | Each of the test antibodies may either be printed in duplicate or as single spots (for a panel of 16 tests) |

The arrays are printed in 5×5 grids as shown in Table 5 below. Test and control antibodies are printed at concentrations ranging from 0.1 mg/ml to 1 mg/ml depending upon the affinity of the antibody for its antigen and the signal obtained from the control antibodies.

TABLE 5

Antibody Array Design for Antigen Detection

| Fiduciary Marker | Test antibody 1 | Test antibody 1 | Test antibody 2 | Test antibody 2 |
|---|---|---|---|---|
| Print Buffer (negative control) | Test antibody 3 | Test antibody 3 | Test antibody 4 | Test antibody 4 |
| Hapten-Conjugated Antibody (Assay Performance (3)) | Test antibody 5 | Test antibody 5 | Test antibody 6 | Test antibody 6 |
| Print Buffer (Negative Control) | Test antibody 7 | Test antibody 7 | Test antibody 8 | Test antibody 8 |
| HRP-Hapten BP Conjugate (Colourimetric Control) | Anti-IgG antibody (assay performance (1)) | Anti-Mouse antibody (assay performance (2)) | Non-Specific antibody (assay specificity) | Fiduciary marker |

Printed arrays are used for measuring the presence of marker proteins by initially incubating with Blocker at 37° C. for 60 min.

Up to ninety-six different samples to be tested such as serum, plasma or any other biological material are added to their own well. Samples may be added without dilution or may be diluted in Blocker prior to addition to the test well.

The membrane is incubated at 37° C. for 60 min, and non-bound material is washed off with PBS-T.

Antigens or ligands bound to arrayed antibodies are detected by sequential incubations with biotinylated secondary antibodies and a biotin-binding protein-conjugated to an enzyme. The amount of enzyme at each spot is then measured by using a substrate that results in a colored precipitate deposited at the spot.

In this example, positive controls are processed and detected as follows. The colourimetric control is processed to generate a colour result by addition of the enzyme substrate. The assay performance controls are processed as follows. Assay performance control (1), an anti-IgG antibody, will bind IgG (a non-target analyte) present in the serum sample. IgG binding will be detected using a secondary antibody, either an antibody-adapter conjugate (e.g., an anti-IgG antibody-biotin conjugate) or an antibody-enzyme conjugate (e.g., an antibody-HRP conjugate). Assay performance control (2), an anti-mouse antibody, will bind the biotinylated secondary antibody. This interaction will then be detected by addition of the biotin binding protein-enzyme conjugate and enzyme substrate or a biotin-binding molecule conjugated to a colored moiety such as colloidal gold. Assay performance control (3), an antibody-biotin conjugate, will bind the biotin binding protein-enzyme conjugate and this interaction will be detected by addition of the enzyme substrate.

Example 4

Antigen Arrays for Antibody Detection

Arrays for detection of antibodies to antigens of interest such as protein markers of autoimmune diseases, cardiovascular diseases, cancer and infectious agents, or ligands such as growth factors, hormones, cytokines and chemokines are created by printing panels of antigens or ligands as capture elements for specific capture of antibodies. A series of control antibodies and control proteins are also printed. These controls serve a variety of functions including controls for monitoring assay performance, including the performance of individual reagents, controls for monitoring the specificity of the assay and fiduciary markers for gridding the arrays after sample processing for determination of signal intensity at each spot in the array. Table 6 summarizes the reagents that may be used to print and process antigen arrays.

TABLE 6

Antigen Array Reagents

| Reagent | Function | Example | Comments |
| --- | --- | --- | --- |
| Protein or Antibody with a Chromogenic Dye | Fiduciary marker to enable the gridding software to locate and place grids on each spot of the array | BlueRanger dye conjugated protein marker | |
| Print Buffer | Negative control for determining the background signal in the array | | |
| Anti-IgM Antibody | Control to demonstrate the addition of sample (assay performance (1)) | Anti-human IgM | Addition of serum will result in binding of serum IgM to this spot; If non-human sample is to be tested the antibody will be replaced with one appropriate for capture of IgG from the species being tested |
| Hapten Binding Protein- Enzyme Conjugate | Positive colourimetric control to monitor the performance of the enzyme substrate | Streptavidin- horseradish peroxidase | |
| Anti- IgG Antibody | Control to demonstrate the addition of sample (assay performance (1)) | | Addition of serum will result in binding of serum IgG to this spot; If non-human sample is to be tested the antibody will be replaced with one appropriate for capture of IgG from the species being tested |
| IgG | Control to demonstrate the addition of secondary detection antibody (assay performance (2)) | Human IgG | The secondary antibody will bind the IgG; If non-human sample is to be tested the antibody will be replaced with one appropriate for capture of IgG from the species being tested |
| Non-Specific Antibody | Negative control for determining antigen capture specificity (assay specificity) | Hamster IgG | IgG from a species not represented in the array panel and detection reagents |
| Panel of Test Antigens or Ligands for Capture of Antibody | Diagnostic tests for disease or wellness markers (capture elements) | Influenza A antigen | Each of the test antigens may either be printed in duplicate or as single spots (for a panel of 16 tests) |

The arrays are printed in 5×5 grids as shown in Table 7 below. Control antibodies are printed at concentrations ranging from 0.1 mg/ml to 1 mg/ml depending upon the signal obtained from the control antibodies. Test antigens or ligands are printed at concentrations ranging from 0.05 mg/ml to 1 mg/ml depending on the affinity of the antigen to test antibodies from positive control biological samples.

TABLE 7

Antigen Array Design for Antibody Detection

| | | | | |
|---|---|---|---|---|
| Fiduciary Marker | Test antigen 1 | Test antigen 1 | Test antigen 2 | Test antigen 2 |
| Print Buffer (Negative Control) | Test antigen 3 | Test antigen 3 | Test antigen 4 | Test antigen 4 |
| Anti-IgM Antibody (Assay Performance (1)) | Test antigen 5 | Test antigen 5 | Test antigen 6 | Test antigen 6 |
| Print Buffer (Negative Control) | Test antigen 7 | Test antigen 7 | Test antigen 8 | Test antigen 8 |
| HRP-Conjugated Protein (Colourimetric Control) | Anti-IgG antibody (assay performance (1)) | IgG (assay performance (2)) | Antibody from non-crossreactive species (assay specificity) | Fiduciary marker |

Printed arrays are used for measuring the presence of antibodies by initially incubating with Blocker at 37° C. for 60 min.

Up to ninety-six different samples to be tested such as serum, plasma or any other biological material are added to their own well. Samples may be added without dilution or may be diluted in Blocker prior to addition to the test well. The membrane is incubated at 37° C. for 60 min, and non-bound material is washed off with PBS-T.

Antibodies bound to arrayed antigens are detected by incubations with enzyme conjugated secondary antibodies or secondary antibodies conjugated to a colored molecule such as colloidal gold. The amount of enzyme at each spot is then measured by using a substrate that results in a colored precipitate deposited at the spot.

Positive controls are detected as follows. The colourimetric control was detected by addition of enzyme substrate. The assay performance (1) control will bind IgG in the serum sample and is detected by addition of a secondary antibody-enzyme conjugate and the enzyme substrate. The assay performance (2) control will bind the secondary antibody-enzyme conjugate and is detected by addition of the enzyme substrate. The assay performance (1) control will bind IgM in the serum sample and is detected by addition of a secondary antibody-enzyme conjugate and the enzyme substrate.

Example 5

Antibody Arrays for Detection of Serum Cytokines

The reagents listed in Table 8 were used for manufacturing and processing of cytokine arrays.

TABLE 8

Cytokine Array Reagents

| Reagent | Vendor | Catalog No. | Function |
|---|---|---|---|
| Mouse anti-human IFNγ antibody | BioLegend | 507501 | Capture elements |
| Mouse anti-human TNFα antibody | BioLegend | 502801 | |
| Mouse anti-human IL4 antibody | BioLegend | 500701 | |
| Goat anti-human IgG antibody | Pierce | 31119 | Detect sample addition, (assay performance (1)) |
| Mouse anti-human IgM antibody | BioLegend | 314501 | |
| Biotin anti-human IFNγ antibody | BioLegend | 502503 | Secondary antibodies |
| Biotin anti-humanTNFα antibody | BioLegend | 502903 | |
| Biotin anti-human IL4 antibody | BioLegend | 500803 | |
| Biotin anti-human IgG antibody | Pierce | 31774 | Detect IgG and IgM binding to the assay performance (1) control |
| Biotin anti-human IgM antibody | BioLegend | 314503 | |
| Streptavidin- horseradish peroxidase | Pierce | 21126 | Colour reaction |
| Goat anti-human IgG horseradish peroxidase | Pierce | 31412 | Fiduciary marker and colour reaction |
| Human IgG | Pierce | 31154 | Assay specificity |
| Human IgM | Pierce | 31146 | |

The arrays were printed in 5×5 grids as shown in Table 6 below. Anti-cytokine antibodies were printed at 0.2 mg/ml and the control antibodies were printed at the concentrations indicated in Table 9. An assay performance control for the secondary antibody was not used.

TABLE 9

Antibody Array Detection for Cytokine Detection

| | | | | |
|---|---|---|---|---|
| Anti-human IgG-peroxidase (50 µg/ml) (fiduciary marker) | Anti-human IgG antibody (assay performance (1)) (200 µg/ml) | Anti-human IgG antibody (assay performance (1)) (200 µg/ml) | Anti-human IgM antibody (assay performance (1) (200 µg/ml) | Anti-human IgM antibody (assay performance (1) (200 µg/ml) |
| Print Buffer (negative control) | Anti-human IFNγ antibody (capture element) (200 µg/ml) | Anti-human IFNγ antibody (capture element) (200 µg/ml) | Anti-human TNFα antibody (capture element) (200 µg/ml) | Anti-human TNFα antibody (capture element) (200 µg/ml) |
| Biotinylated anti-human IgG- (assay performance (3)) 50 µg/ml | Anti-human IL4 antibody (capture element) (200 µg/ml) | Anti-human IL4 antibody (capture element) (200 µg/ml) | Print Buffer (negative control) | Print Buffer (negative control) |
| Print Buffer (negative control) | Print Buffer (negative control) | Print Buffer (negative control) | Print Buffer (negative control) | Print Buffer (negative control) |
| Streptavidin-peroxidase (colourimetric control) (400 µg/ml) | Human IgG (50 µg/ml) (assay performance (2)) | Human IgG (50 µg/ml) (assay performance (2)) | Human IgM (50 µg/ml) (assay performance (2)) | Anti-human IgG-peroxidase (50 µg/ml) (fiduciary marker) |

Printed arrays were used for measuring the amount of cytokines by initially incubating with Blocker at 37° C. for 60 min.

Human serum spiked with known amounts of cytokines was added to each of the ninety-six arrays on the membrane plate. The membrane was incubated at 37° C. for 60 min, and non-bound material was washed off with PBS-T.

Cytokines bound to arrayed antibodies were detected by sequential incubations with biotinylated anti-cytokine antibodies and streptavidin-conjugated horseradish peroxidase. Positive controls were detected by incubating with biotinylated anti-human IgG and anti-human IgM antibodies before streptavidin-HRP was added. The amount of peroxidase in each spot was then measured by using metal enhanced diaminobenzidine.

In this experiment, assay performance (2) antibodies on the array detected the secondary antibodies for resolving the assay performance (1) control (i.e., the biotinylated anti-human IgG and anti-human IgM antibodies), rather than being antibodies that detected the biotinylated anti-human cytokine antibodies preferred in Example 3.

Figure 3:
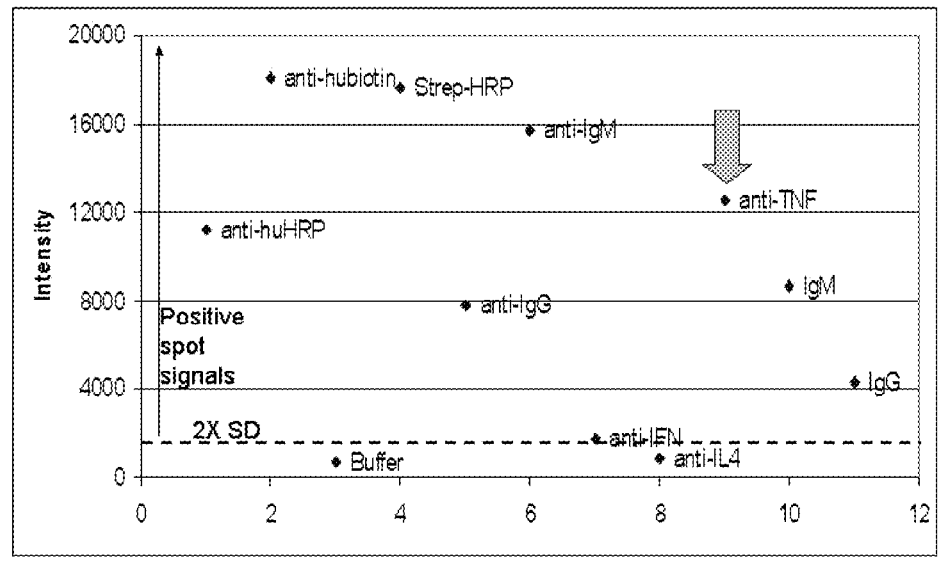
FIG. 3 is a graphical diagram summarizing the results of Example 5 obtained from processing human serum spiked with cytokines. The hash line represents the threshold signal above which the result is considered positive. The threshold is set at two times the signal intensity of the negative control spot (the Buffer spot).

A representative example of the results obtained from processing a human serum sample spiked with TNFα at 1.25 µg/ml and IFNγ at 0.32 ng/ml is shown in FIG. 3. The hash line represents the threshold signal above which the result is considered positive. The threshold is based on the signal intensity of negative control spots and is two times the signal. The data is also shown in Table 10 for the samples tested.

TABLE 10

Results of Example 5

| Sample Number | Test | Result | Comment |
|---|---|---|---|
| 1 | IgG | Positive | Sample was serum |
| | IgM | Positive | Sample was serum |
| | IFNγ | Positive | Cytokine present |
| | TNFα | Positive | Cytokine present |
| | IL4 | Negative | Not present |

Example 6

Antigen Arrays for Detection of Antibodies in Samples Reactive to Infectious Disease Antigens The reagents listed in Table 11 were used for manufacturing and processing of antigen arrays.

TABLE 11

Antibody Detection Assay Reagents

| Reagent | Vendor | Catalog No. | Function |
|---|---|---|---|
| Anti-mouse antibody peroxidase | Pierce | 31430 | Colour reaction |
| Recombinant Hepatitis B core antigen | BiosPacific | J44400352 | Capture elements |
| Recombinant Hepatitis B surface antigen, ad | BiosPacific | J44050228 | |
| Recombinant Hepatitis B surface antigen, ay | BiosPacific | J44030228 | |
| Mouse anti-Hepatitis B antibody, reactive to ad and ay subtype | BiosPacific | A34060259P | |
| CMV E1A IgG antigen | BiosPacific | J43010230 | |
| CMV E1A IgM antigen | BiosPacific | J43020230 | |
| Influenza A antigen | BiosPacific | J43610149 | |
| Influenza B antigen | BiosPacific | J43620149 | |

TABLE 11-continued

Antibody Detection Assay Reagents

| Reagent | Vendor | Catalog No. | Function |
|---|---|---|---|
| Goat anti-human IgG horseradish peroxidase | Pierce | 31412 | Fiduciary marker and colour reaction |
| Goat anti-human IgM horseradish peroxidase | Pierce | 31415 | Colour reaction |
| Goat anti-human IgG antibody | Pierce | 31119 | Detect sample addition, (assay performance (1)) Detect IgG and IgM binding to the assay performance (1) control |
| Mouse anti-human IgM antibody | BioLegend | 314501 | |
| Human IgG | Pierce | 31154 | Detect detection antibody addition, (assay performance (1)) |
| Goat IgG | Pierce | 31212 | Assay specificity |

The arrays were printed in 5×5 grids. Control antibodies and the recombinant or purified antigens were printed at various concentrations as shown in Table 12.

TABLE 12

Antigen Assay Design for Antibody Detection

| Anti-human IgG-peroxidase 50 μg/ml | CMV E1A IgG Ag 0.5 mg/ml | CMV E1A IgG Ag 0.5 mg/ml | CMV E1A IgM Ag 0.5 mg/ml | CMV E1A IgM Ag 0.5 mg/ml |
|---|---|---|---|---|
| Print Buffer | Hepatitis B surface Ag ad 0.25 mg/ml | Hepatitis B surface Ag ad 0.25 mg/ml | Hepatitis B surface Ag ay 0.25 mg/l | Hepatitis B surface Ag ay 0.25 mg/ml |
| Anti-human IgM antibody | Influenza A Ag 0.25 mg/ml | Influenza A Ag 0.25 mg/ml | Influenza B Ag 0.25 mg/ml | Influenza B Ag 0.25 mg/ml |
| Print Buffer | Hepatitis B core Ag 0.25 mg/ml | Hepatitis B core Ag 0.25 mg ml | Print Buffer | Print Buffer |
| Anti-human IgG-peroxidase 50 μg/ml | Anti-human IgG antibody 0.2 mg/ml | Human IgG 0.01 mg/ml | Goat IgG 0.2 mg/ml | Anti-human IgG-peroxidase 50 μg/ml |

Printed arrays were initially incubated with Blocker at 37° C. for 60 min.

Human serum spiked with 10 μg/ml of anti-Hepatitis B antibodies reactive to ad and ay subtypes were added to Row A of the plate containing the arrays and diluted 2-fold in Blocker from Row A to G. Row H contained only the Blocker solution. The membrane was incubated at 37° C. for 60 min, and non-bound antibodies were washed off with PBS-T.

Antibodies bound to arrayed antigens were detected by incubation with a mixture of horseradish peroxidase-conjugated anti-mouse IgG antibody, and anti-human IgG and IgM antibodies. The amount of peroxidase in each spot was then measured by using metal enhanced diaminobenzidine.

Figure 4:
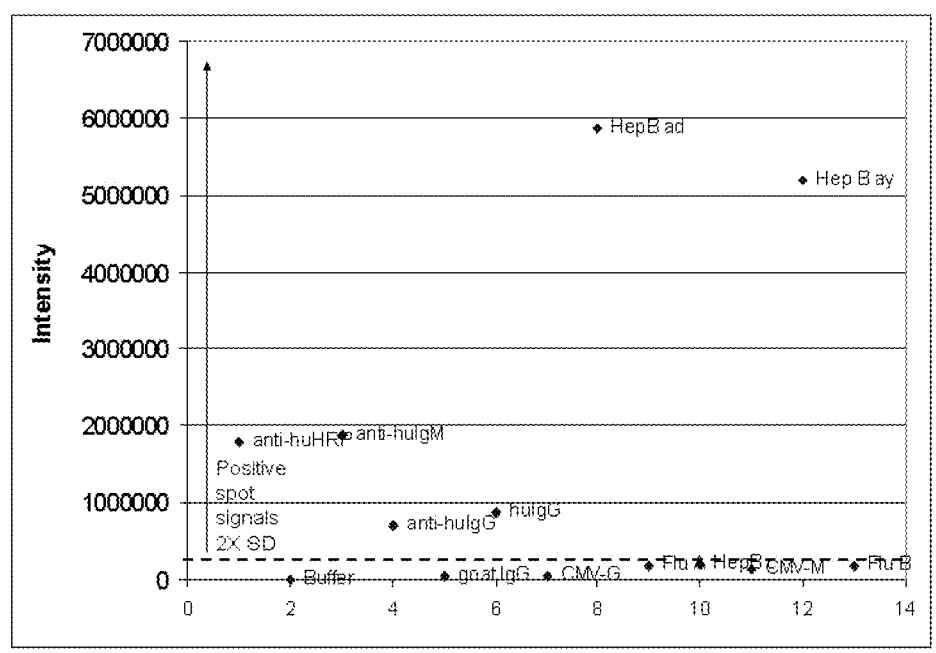
FIG. 4 is a graphical diagram summarizing the results Example 6 obtained from processing human serum sample spiked with antibodies to Hepatitis B surface antigens. The hash line represents the threshold signal above which the result is considered positive. The threshold is set at two times the signal intensity of the negative control spot (the Buffer spot).

As shown in FIG. 4, the assay returned a positive signal for the presence of anti-Hepatitis B antibodies reactive to ad and ay subtypes. The signal from the other antigens was below the threshold for a positive tests result, highlighting the specificity of the array.

Example 7

Optimization of Print Concentration of Fiduciary Marker

50 μl of the Print buffer was added to each of three tubes of lyophilized BlueRanger Prestained Protein Molecular Weight Marker (Pierce, Catalog No. 26681). The three protein solutions were pooled and transferred to a microfuge tube labeled Tube 1. Four other microfuge tubes were labeled from 2 to 5 and 62 μl of Print buffer was added to each tube.

The prestained protein was diluted 2-fold from tubes 1 to 5 and used for printing arrays. The array configuration is shown in Table 13.

TABLE 13

Array Configuration

| Undiluted prestained protein | Undiluted prestained protein |
|---|---|
| 1 in 2 dilution of protein | 1 in 2 dilution of protein |
| 1 in 4 dilution of protein | 1 in 4 dilution of protein |
| 1 in 8 dilution of protein | 1 in 8 dilution of protein |
| 1 in 16 dilution of protein | 1 in 16 dilution of protein |

Figure 5:
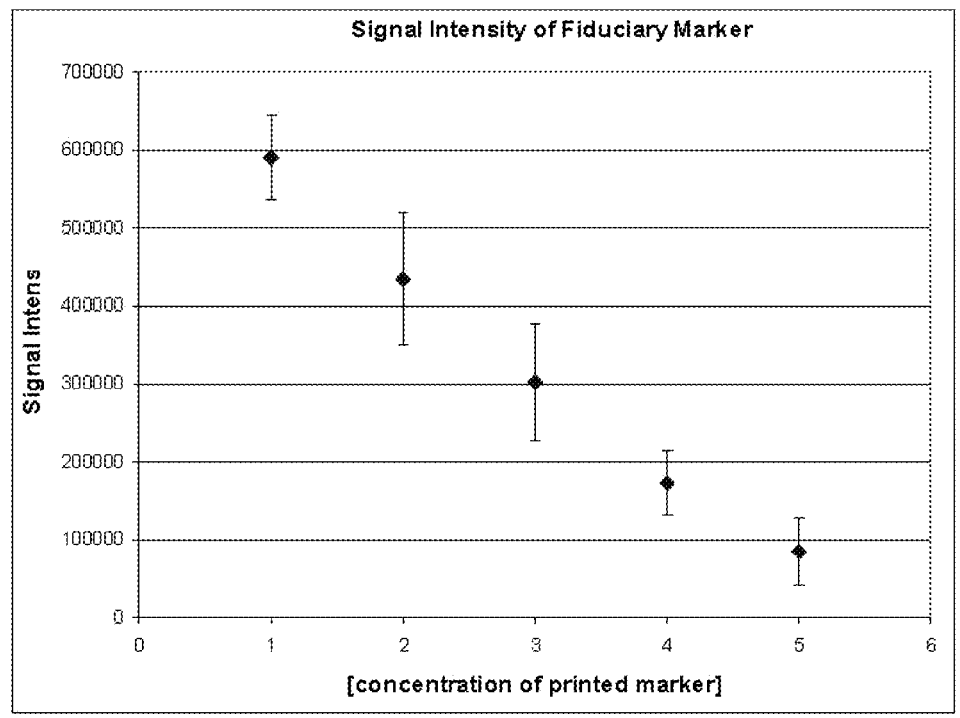
FIG. 5 is a graphical diagram summarizing the results of Example 7 that assess the efficacy of a fiduciary marker of one embodiment of the invention. The x-axis units identify the tube number and thus the dilution factor.

The arrays were scanned and analyzed and the results are shown in FIG. 5, where the x-axis units identify the tube and thus the dilution factor.

Example 8

Allergen Arrays for Anti-IgE Antibody Detection

Arrays for detection of IgE antibodies to allergens of interest such as those obtained by recombinant methods or derived from, e.g., dust mites, grass and tree pollen, animal dander, moulds, insect venoms and foods such as soy protein, milk proteins, proteins derived from varieties of nuts, cereals and legumes, proteins from seafood such as shrimp, abalone and lobsters and others are created by printing panels of allergens as capture elements for specific capture of IgE antibodies. A series of control antibodies and control proteins are also printed. These controls serve a variety of functions including controls for monitoring assay performance, including the performance of individual reagents, controls for monitoring the specificity of the assay and fiduciary markers for gridding the arrays after sample processing for determination of signal intensity at each spot in the array. Table 14 summarizes exemplary reagents that may be used to print and process allergen arrays.

TABLE 14

Allergen Array Reagents

| Reagent | Function | Example | Comments |
| --- | --- | --- | --- |
| Protein or antibody conjugated with a chromogenic dye or enzyme | Fiduciary marker to enable the gridding software to locate and place grids on each spot of the array | BlueRanger dye conjugated protein marker or antibody-horse-radish peroxidase conjugate | |
| Print Buffer | Negative control for determining the background signal in the array | | |
| Anti-IgE antibody (Assay performance control 1) | Determine presence of total IgE in sample | Mouse anti-human IgE antibody | Presence of IgE in serum will result in binding of IgE to this spot; If non-human sample is to be tested the antibody will be replaced with one appropriate for capture of IgE from the species being tested |
| Hapten binding protein- enzyme conjugate | Positive colorimetric control to monitor the performance of the enzyme substrate | Streptavidin-horseradish peroxidase | |
| Anti- human IgG antibody (assay performance control 1) | Control to demonstrate the addition of sample | | Addition of serum will result in binding of serum IgG to this spot; If non-human sample is to be tested the antibody will be replaced with one appropriate for capture of IgG from the species being tested |
| IgE (Assay performance control 2) | Control to demonstrate the addition of secondary detection antibody | Human IgE | The secondary antibody will bind the IgE; If non-human sample is to be tested the antibody will be replaced with one appropriate for capture of anti-IgE for the species being tested |
| Non-specific antibody | Negative control for determining antigen capture specificity (assay specificity) | Hamster IgG | IgG from a species not represented in the array panel and detection reagents |
| Panel of test allergens for capture of antibody | Diagnostic tests to determine specificity of patient IgE to allergen (capture elements) | Dust mite extract | Each of the test allergens may either be printed in duplicate or as single spots (for a panel of 16 tests) |

The arrays are printed in 5×5 grids as shown in Table 15. Control antibodies are printed at concentrations ranging from 0.1 mg/ml to 1.0 mg/ml depending upon the signal obtained from the control antibodies. Test allergens are printed at concentrations ranging from 0.05 mg/ml to 1.0 mg/ml depending on the affinity of the antigen to test antibodies from positive control biological samples.

TABLE 15

Allergen Array Design for IgE Antibody Detection

| | | | | |
|---|---|---|---|---|
| Fiduciary marker | Test allergen 1 | Test allergen 1 | Test allergen 2 | Test allergen 2 |
| Print Buffer (negative control) | Test allergen 3 | Test allergen 3 | Test allergen 4 | Test allergen 4 |
| Anti-IgE antibody (assay performance (1)) | Test allergen 5 | Test allergen 5 | Test allergen 6 | Test allergen 6 |
| Print Buffer (negative control) | Test allergen 7 | Test allergen 7 | Test allergen 8 | Test allergen 8 |
| HRP-conjugated protein (colorimetric control) | Anti-human IgG antibody (assay performance (1)) | IgE (assay performance (2)) | Antibody from non-crossreactive species (assay specificity) | Fiduciary marker |

Printed arrays are used for measuring the presence of antibodies by initially incubating with Blocker at 37° C. for 60 min.

Up to ninety-six different samples to be tested (e.g., serum or plasma) may be added to the individual wells. Samples may be added without dilution or may be diluted in Blocker prior to addition to the test well. The membrane is incubated at 37° C. for 60 min, and non-bound material is washed off with PBS-T.

Antibodies bound to arrayed antigens are detected by incubations with enzyme conjugated secondary antibodies or secondary antibodies conjugated to a colored molecule such as colloidal gold. The amount of enzyme at each spot is then measured by using a substrate that results in a colored precipitate deposited at the spot. Positive controls are detected as follows: The colorimetric control was detected by addition of enzyme substrate. The assay performance control (1) will bind IgG in the serum sample and is detected by addition of a secondary antibody-enzyme conjugate and the enzyme substrate. The assay performance (2) control will bind the secondary antibody-enzyme conjugate and is detected by addition of the enzyme substrate. The assay performance (1) control will bind IgE in the serum sample and is detected by addition of a secondary antibody-enzyme conjugate and the enzyme substrate.

Example 9

Composite Antibody and Antigen Arrays

Arrays for simultaneous detection of presence of antibodies and antigens such as cytokines and other protein biomarkers in serum are created by printing panels of corresponding cognate antigens and antibodies as capture elements for specific capture of analytes. A series of control antibodies and control proteins are also printed. These controls serve a variety of functions, such as monitoring assay performance, including the performance of individual reagents, monitoring the specificity of the assay, and fiduciary markers for gridding the arrays after sample processing for determination of signal intensity at each spot in the array. Table 16 summarizes exemplary reagents that may be used to print and process these composite arrays.

TABLE 16

Composite Antibody and Antigen Array Reagents

| Reagent | Function | Example | Comments |
|---|---|---|---|
| Protein or antibody conjugated with a chromogenic dye or enzyme | Fiduciary marker to enable the gridding software to locate and place grids on each spot of the array | BlueRanger dye conjugated protein marker or antibody-horseradish peroxidase conjugate | |
| Print Buffer | Negative control for determining the background signal in the array | | |

TABLE 16-continued

Composite Antibody and Antigen Array Reagents

| Reagent | Function | Example | Comments |
| --- | --- | --- | --- |
| Anti-secondary antibody IgG (Assay performance control 3) | Monitor performance of secondary detection antibodies | Goat anti-mouse IgG antibody | Addition of secondary antibody will result in binding of IgG to this spot; the antibody spotted will vary depending upon the contents of the secondary antibody cocktail. |
| Hapten binding protein- enzyme conjugate | Positive colorimetric control to monitor the performance of the enzyme substrate | Streptavidin-horseradish peroxidase | |
| Anti- human IgG antibody (assay performance control 1) | Control to demonstrate the addition of sample | | Addition of serum will result in binding of serum IgG to this spot; If non-human sample is to be tested the antibody will be replaced with one appropriate for capture of IgG from the species being tested |
| IgG (Assay performance control 2) | Control to demonstrate the addition of secondary detection antibody | Human IgG | The secondary antibody will bind the IgG; If non-human sample is to be tested the antibody will be replaced with one appropriate for capture of IgG from the species being tested |
| Non-specific antibody | Negative control for determining antigen capture specificity (assay specificity) | Hamster IgG | IgG from a species not represented in the array panel and detection reagents |
| Panel of test antigens for capture of antibody | Diagnostic tests to determine specificity of patient IgG or IgM to antigen (capture elements) | anti-nuclear antigen (ANA) | Each of the test antigens may either be printed in duplicate or as single spots (for a panel of 16 tests) |
| Panel of test antibodies for binding to antigens | Diagnostic tests to determine presence of antigens in patient samples (capture elements) | C-reactive protein | Each of the test antibodies may either be printed in duplicate or as single spots (for a panel of 16 tests) |

The arrays are printed in 5×5 grids as shown in Table 17. Control antibodies are printed at concentrations ranging from 0.1 mg/ml to 1.0 mg/ml depending upon the signal obtained from the control antibodies. Test antigens and antibodies are printed at concentrations ranging from 0.05 mg/ml to 1.0 mg/ml depending on the affinity of the antigen to test antibodies from positive control biological samples.

TABLE 17

Composite Antibody and Antigen Arrays

| Fiduciary marker | Test antigen 1 | Test antigen 1 | Test antigen 2 | Test antigen 2 |
| --- | --- | --- | --- | --- |
| Print Buffer (negative control) | Test antigen 3 | Test antigen 3 | Test antigen 4 | Test antigen 4 |
| Anti-secondary antibody IgG (assay performance (3)) | Test antibody 1 | Test antibody 1 | Test antibody 2 | Test antibody 2 |
| Print Buffer (negative control) | Test antibody 3 | Test antibody 3 | Test antibody 4 | Test antibody 4 |
| HRP-conjugated protein (colorimetric control) | Anti-human IgG antibody (assay performance (1)) | IgG (assay performance (2)) | Antibody from non-crossreactive species (assay specificity) | Fiduciary marker |

Printed arrays are used for measuring the presence of antigens and antibodies by initially incubating with Blocker at 37° C. for 60 min.

Up to ninety-six different samples to be tested such as serum or plasma are added to individual wells. Samples may be added without dilution or may be diluted in Blocker prior to addition to the test well. The membrane is incubated at 37° C. for 60 min, and non-bound material is washed off with PBS-T.

Antigens and Antibodies bound to arrayed reagents are detected by incubations with enzyme conjugated secondary antibodies or secondary antibodies conjugated to a colored molecule such as colloidal gold. The amount of enzyme at each spot is then measured by using a substrate that results in a colored precipitate deposited at the spot. Positive controls are detected as follows. The colorimetric control was detected by addition of enzyme substrate. The assay performance control (1) will bind IgG in the serum sample and is detected by addition of a secondary antibody-enzyme conjugate and the enzyme substrate. The assay performance (2) control will bind the secondary antibody-enzyme conjugate and is detected by addition of the enzyme substrate. The assay performance (3) control will bind secondary IgG (detection antibodies) and is detected by addition of a detection antibody-enzyme conjugate and the enzyme substrate.

Example 10

Upper Respiratory Viral Pathogen Arrays for Detection of Antibodies in Serum Samples The reagents listed in Table 18 were used for manufacturing and processing of antigen arrays.

TABLE 18

Antibody Detection Assay Reagents

| Reagent | Vendor | Catalog No. | Function |
| --- | --- | --- | --- |
| Anti-mouse antibody peroxidase | Pierce | 31430 | Colour reaction |
| Adenovirus antigen | Virion | 1121 | Capture elements |
| Cytomegalovirus CF antigen | Virion | 1130 | |
| Influenza A antigen | Microbix | EL-13-02 | |
| Influenza B antigen | Microbix | EL-14-02 | |
| Parainfluenza 3 antigen | Microbix | EL-10-02 | |
| Respiratory Syncytial Virus antigen | Virion | 1124 | |
| Cytomegalovirus IgG antigen | BioSPacific | J43010230 | |
| Influenza A antigen | BioSPacific | J43610149 | |
| Goat anti-human IgG horseradish peroxidase | Pierce | 31412 | Fiduciary marker and colour reaction |
| Goat anti-human IgG antibody | Pierce | 31119 | Detect sample addition, (assay performance (1)) |
| Mouse anti-human IgM antibody | BioLegend | 314501 | Detect IgG and IgM binding to the assay performance (1) control |
| Human IgG | Pierce | 31154 | Detect detection antibody addition, (assay performance (2)) |
| Mouse IgG | Pierce | 31202 | Assay specificity |
| Goat anti-mouse IgG | Pierce | 31164 | Assay specificity |

The arrays were printed in 5×5 grids. Control antibodies and the recombinant or purified antigens were printed at various concentrations as shown in Table 19.

TABLE 19

Upper Respiratory Viral Pathogen Assay Design for Antibody Detection

| | | | | |
| --- | --- | --- | --- | --- |
| Anti-mouse IgG-peroxidase 0.1 mg/ml | Adenovirus Ag 2-fold dilution | Adenovirus Ag 2-fold dilution | CMV CF Ag 2-fold dilution | CMV CF Ag 2-fold dilution |
| Print Buffer | Influenza A Ag (Microbix) 0.50 mg/ml | Influenza A Ag (Microbix) 0.50 mg/ml | Influenza B Ag 0.40 mg/ml | Influenza B Ag 0.40 mg/ml |
| Anti-mouse IgG antibody 0.05 mg/ml | Parainfluenza 3 Ag 1.0 mg/ml | Parainfluenza 3 Ag 1.0 mg/ml | RSV Ag 2-fold dilution | RSV Ag 2-fold dilution |
| Print Buffer | CMV E1A IgG Ag 0.40 mg/ml | CMV E1A IgG Ag 0.40 mg/ml | Influenza A Ag (Biospacific) 0.40 mg/ml | Influenza A Ag (BiosPacific) 0.40 mg/ml |
| human IgG 0.01 mg/ml | mouse IgG 0.01 mg/ml | Anti- Human IgG 0.025 mg/ml | Anti- Human IgM 0.1 mg/ml | Anti-mouse IgG-peroxidase 0.1 mg/ml |

Printed arrays were initially incubated with Blocker at 37° C. for 60 min. Human serum samples were added at a 1 in 100 dilution to Row A of the plate containing the arrays and diluted 2-fold in Blocker from Row A to G. Row H contained only the Blocker solution. The membrane was incubated at 37° C. for 60 min, and non-bound antibodies were washed off with PBS-T.

Antibodies bound to arrayed antigens were detected by incubation with horseradish peroxidase-conjugated anti-mouse IgG antibody. The amount of peroxidase in each spot was then measured by using metal enhanced diaminobenzidine.

Figure 6:
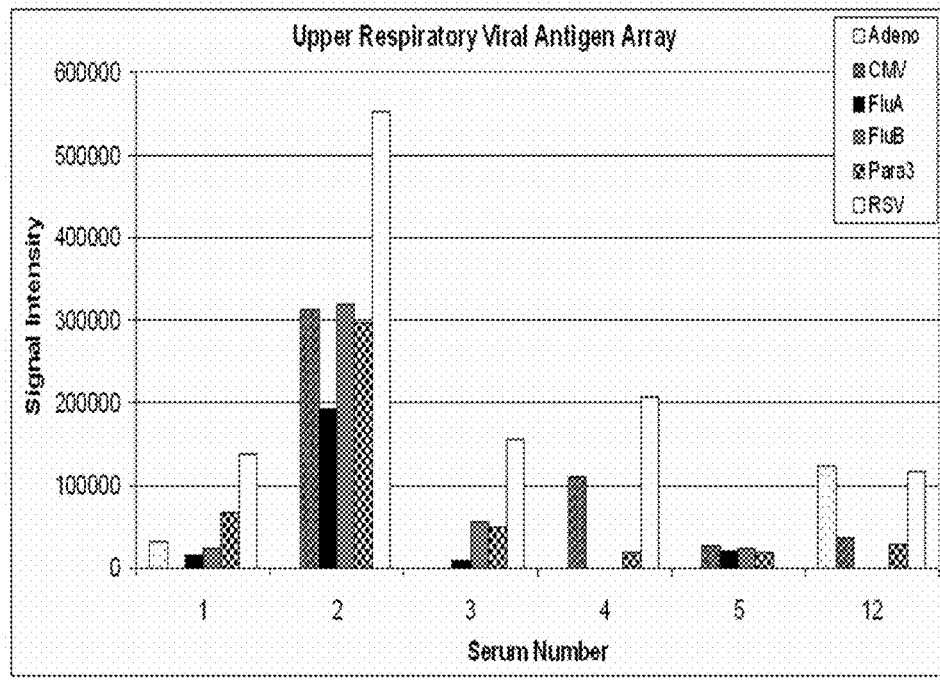
FIG. 6 is a graphical diagram showing the results of Example 10 that demonstrate upper respiratory viral pathogen arrays for detection of antibodies in serum samples. Six human serum samples were tested at a dilution of 1 in 800 for presence of antibodies to each of the six viral antigens on arrays. A signal intensity threshold of 100000 was set for a positive test. Based on this threshold the results shown in Table 20 were obtained.

FIG. 6 shows the results of six human serum samples at a dilution of 1 in 800 for presence of antibodies to each of the six viral antigens on arrays. A signal intensity threshold of 100000 was set for a positive test. The assay returned a positive signal for some of the antigens on the array. The signal from the other antigens was below the threshold for a positive tests result, highlighting the ability of the arrays to determine the presence of serum antibodies to the arrayed antigens. Based on this threshold the results shown in Table 20 were obtained.

TABLE 20

| Sample | Adeno | CMV | Flu A | Flu B | Para3 | RSV |
| --- | --- | --- | --- | --- | --- | --- |
| 1 | Negative | Negative | Negative | Negative | Negative | Positive |
| 2 | Negative | Positive | Positive | Positive | Positive | Positive |
| 3 | Negative | Negative | Negative | Negative | Negative | Positive |
| 4 | Negative | Positive | Negative | Negative | Negative | Positive |
| 5 | Negative | Negative | Negative | Negative | Negative | Negative |
| 12 | Positive | Negative | Negative | Negative | Negative | Positive |

Example 11

Hepatitis B Antigen Arrays for Detection of Anti-Hepatitis B Antibodies in Serum Samples The reagents listed in Table 21 were used for manufacturing and processing of antigen arrays.

TABLE 21

Anti-Hepatitis B antibody Detection Assay Reagents

| Reagent | Vendor | Catalog No. | Function |
| --- | --- | --- | --- |
| Anti-mouse antibody peroxidase | Pierce | 31430 | Colour reaction |
| Hepatitis B surface antigen "ad" | BiosPacific | J44010031 | Capture elements |
| Hepatitis B surface antigen "ay" | BiosPacific | J44020031 | |
| Hepatitis B "E" antigen | BiosPacific | J44200352 | |
| Hepatitis B core antigen | BiosPacific | J44400352 | |
| Goat anti-human IgG horseradish peroxidase | Pierce | 31412 | Fiduciary marker and colour reaction |
| Goat anti-human IgG antibody | Pierce | 31119 | Detect sample addition, (assay performance (1)) Detect IgG and IgM binding to the assay performance (1) control |
| Human IgG | Pierce | 31154 | Detect detection antibody addition, (assay performance (2)) |
| Goat anti-mouse IgG | Pierce | 31164 | Assay specificity |

The arrays were printed in 5×3 grids. Control antibodies and the recombinant or purified antigens were printed at various concentrations as shown in Table 22.

TABLE 22

Antigen Assay Design for Anti-Hepatitis B Antibody Detection

| | | |
| --- | --- | --- |
| Anti-mouse IgG-peroxidase 0.1 mg/ml | Hepatitis B surface antigen "ad" 0.2 mg/ml | Hepatitis B surface antigen "ad" 0.2 mg/ml |
| Print Buffer | Hepatitis B surface antigen "ay" 0.2 mg/ml | Hepatitis B surface antigen "ay" 0.2 mg/ml |
| Anti-mouse IgG antibody 0.2 mg/ml | Hepatitis B "E" antigen 0.2 mg/ml | Hepatitis B "E" antigen 0.2 mg/ml |
| Print Buffer | Hepatitis B core antigen 0.2 mg/ml | Hepatitis B core antigen 0.2 mg/ml |
| Anti-human IgG antibody 0.2 mg/ml | Human IgG 0.05 mg/ml | Anti-mouse IgG-peroxidase 0.1 mg/ml |

Printed arrays were initially incubated with Blocker at 37° C. for 60 min. Human serum samples were added at a 1 in 100 dilution to Row A of the plate containing the arrays and diluted 2-fold in Blocker from Row A to G. Row H contained only the Blocker solution. The membrane was incubated at 37° C. for 60 min, and non-bound antibodies were washed off with PBS-T.

Figure 7:
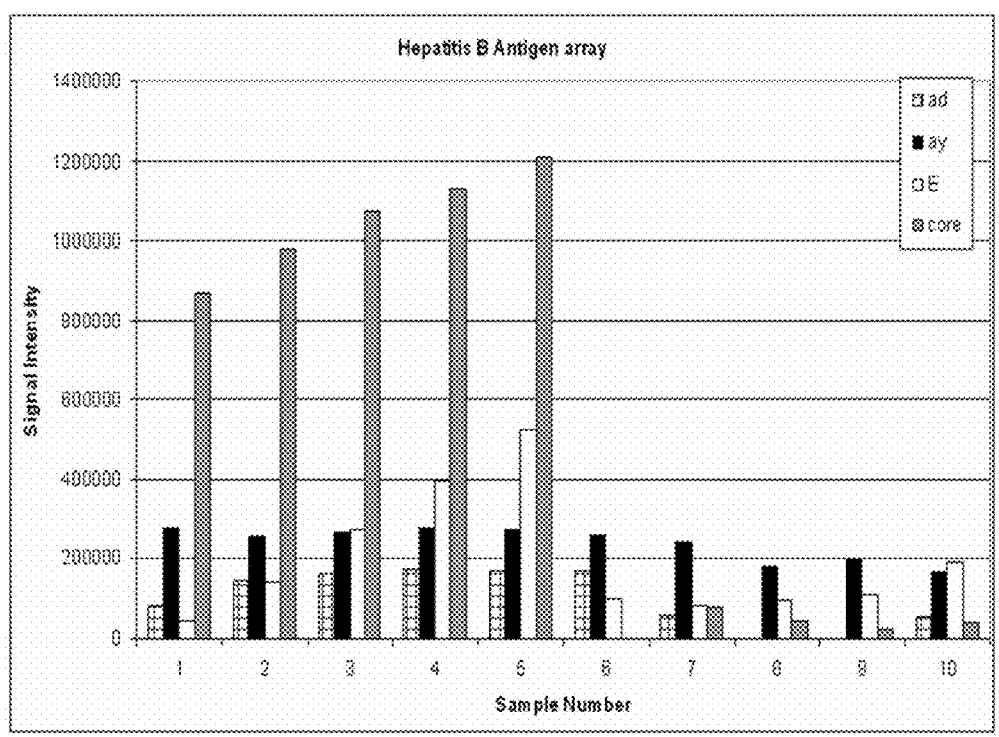
FIG. 7 is a graphical diagram showing the results of Example 11 showing the results from ten human serum samples that were tested at a dilution of 1 in 4000 for presence of antibodies to each of the four Hepatitis B antigens on arrays.

Antibodies bound to arrayed antigens were detected by incubation with horseradish peroxidase-conjugated anti-human IgG antibody. The amount of peroxidase in each spot was then measured by using metal enhanced diaminobenzidine. FIG. 7 shows the results of ten human serum samples tested at a dilution of 1 in 4000 for presence of antibodies to each of the four Hepatitis B antigens on arrays.

Although the invention has been described with reference to the above example, it will be understood that modifications and variations are encompassed within the spirit and scope of the invention. Accordingly, the invention is limited only by the following claims.

What is claimed is:

1. A method of detecting a target analyte comprising:
   a) providing a microtiter plate having a plurality of wells, each well having a microporous membrane, each microporous membrane comprising an array of capture elements printed on the membrane surface, each capture element corresponding to and being able to bind a target analyte, the array further comprising at least one fiduciary marker and two or more control elements selected from the group consisting of:
      i) at least one negative control to monitor background signal,
      ii) at least one negative control to monitor assay specificity,
      iii) at least one positive colourimetric control, and
      iv) at least one positive control to monitor assay performance; and
   b) contacting a microporous membrane of the microtiter plate with a sample such that a target analyte selectively binds a capture element and generates a detectable signal when the target analyte is present in the sample;
   c) processing the microtiter plate using an automated system to detect binding of the target analyte to the capture element, wherein processing comprises:
      i) orienting and gridding the array using the at least one fiduciary marker,
      ii) detecting the at least one positive colourimetric control,
      iii) monitoring assay performance using the at least one positive control, and
      iv) detecting the target analyte by detecting intensity of the detectable signal, thereby detecting the target analyte.

2. The method of claim 1, wherein the array of capture elements comprises a plurality of pairs of capture elements, each capture element in a pair being able to bind the same target analyte, each pair of capture elements being able to bind a different target analyte than any other pair of capture elements.

3. The method of claim 1, wherein the capture elements are antigens.

4. The method of claim 3, wherein the antigens are selected from one or more of *Toxoplasma gondii*, rubella virus, cytomegalovirus, herpes simplex virus type 1 and herpes simplex virus type 2.

5. The method of claim 1, wherein the capture elements are antibodies or fragments thereof.

6. The method of claim 5, wherein the capture elements specifically bind an antigen, wherein the antigen is selected from one or more of *Toxoplasma gondii*, rubella virus, cytomegalovirus, herpes simplex virus type 1 and herpes simplex virus type 2.

7. The method of claim 1, wherein the target analyte is an antibody or fragment thereof.

8. The method of claim 7, wherein the antibody is an IgG or IgM.

9. The method of claim 1, wherein the target analyte is an antigen and the capture elements are antibodies or fragments thereof.

10. The method of claim 9, wherein the antigen is selected from one or more of *Toxoplasma gondii*, rubella virus, cytomegalovirus, herpes simplex virus type 1 and herpes simplex virus type 2.

11. The method of claim 1, wherein the target analyte and capture elements are antigens, or antibodies or fragments thereof.

12. The method of claim 11, wherein the antibodies or fragments thereof specifically bind the antigens, wherein the antigens are selected from one or more of *Toxoplasma gondii*, rubella virus, cytomegalovirus, herpes simplex virus type 1 and herpes simplex virus type 2.

13. The method of claim 1, wherein the microporous membrane is removably attached to a microtiter plate.

14. The method of claim 1, wherein the microporous membrane comprises a plurality of arrays, each having capture elements printed on the membrane surface.

15. The method of claim 1, wherein the capture elements comprise a polypeptide, carbohydrate, oligonucleotide or combination thereof.

16. The method of claim 15, wherein the polypeptide is a glycoprotein.

17. The method of claim 1, wherein the capture elements comprise a ligand.

18. The method of claim 1, wherein the capture elements comprise a biomolecule.

19. The method of claim 1, wherein the target analyte is a polypeptide, carbohydrate, lipid, virus, drug, oligonucleotide or combination thereof.

20. The method of claim 1, wherein the target analyte is an antigen or fragment thereof.

* * * * *